United States Patent

Mossakowska et al.

[11] Patent Number: 5,833,989
[45] Date of Patent: Nov. 10, 1998

[54] SOLUBLE CR1 DERIVATIVES

[75] Inventors: Danuta Ewa Irena Mossakowska, Mountfitchet; Ian Dodd, Buckland; Anne Mary Freeman, Wendover; Richard Anthony Godwin Smith, Horseheath, all of England

[73] Assignee: Adprotech PLC, Royston, United Kingdom

[21] Appl. No.: 356,361

[22] PCT Filed: Jun. 16, 1993

[86] PCT No.: PCT/GB93/01282

§ 371 Date: Mar. 7, 1995

§ 102(e) Date: Mar. 7, 1995

[87] PCT Pub. No.: WO94/00571

PCT Pub. Date: Jan. 6, 1994

[30] Foreign Application Priority Data

Jun. 24, 1992 [GB] United Kingdom .................. 9213376
Mar. 1, 1993 [GB] United Kingdom .................. 9304057

[51] Int. Cl.$^6$ .................. A61K 38/00; C07K 14/435
[52] U.S. Cl. .................. 424/185.1; 424/195.11; 435/69.9; 530/380
[58] Field of Search .................. 424/185.1, 195.11; 530/300, 350, 380, 395; 435/69.3, 69.9

[56] References Cited

U.S. PATENT DOCUMENTS 5,212,071 5/1993 Fearon et al. .................. 435/69.1

FOREIGN PATENT DOCUMENTS

WO 89/09220 10/1989 WIPO .................. C07H 15/12

OTHER PUBLICATIONS

Makrides, et al., J. Biol. Chem., vol. 267, No. 34, pp. 24754–24761 (1992).

Krych, et al., "Sites within the Complement C3b/C4b Receptor Important for the Specificity of Ligand Binding", *Proceedings of the National Academy of Sciences*, 88, No. 10, pp.: 4353–4357 (1991).

Kalli, et al., "Mapping of the C3b–binding Site of CR1 and Construction of a (CR1)2–F(ab)'12 Chimeric Complement Inhibitor", *Biological Abstracts*, 93, Abstract No. 53233 (1992).

*Primary Examiner*—Thomas M. Cunningham
*Attorney, Agent, or Firm*—Foley & Lardner

[57] ABSTRACT

A soluble polypeptide comprising, in sequence, one to four short consensus repeats (SCR) selected from SCR 1, 2, 3 and 4 of long homologous repeat A (LHR-A) as the only structurally and functionally intact SCR domains of CR1 and including at least SCR3.

16 Claims, 3 Drawing Sheets

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
TATGCAGTGC AACGCTCCGG AATGGCTGCC GTTCGCGCGC CCGACCAACC TGACTGATGA      60
ATTTGAGTTC CCGATCGGTA CCTACCT                                         87
```

( 2 ) INFORMATION FOR SEQ ID NO:2:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

```
CGTAGTTCAG GTAGGTACCG ATCGGGAACT CAAATTCATC AGTCAGGTTG GTCGGGCGCG      60
CGAACGGCAG CCATTCCGGA GCGTTGCACT GCA                                  93
```

( 2 ) INFORMATION FOR SEQ ID NO:3:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

```
GAACTACGAA TGCCGCCCGG GTTATAGCGG CCGCCCGTTT TCTATCATCT GCCTGAAAAA      60
CTCTGTCTGG ACTGGTGCTA AGGACCGTTG CCGACGTAAA T                        101
```

( 2 ) INFORMATION FOR SEQ ID NO:4:

( i ) SEQUENCE CHARACTERISTICS:
        ( A ) LENGTH: 101 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:4:

```
ACGACAAGAT TTACGTCGGC AACGGTCCTT AGCACCAGTC CAGACAGAGT TTTTCAGGCA        60
GATGATAGAA AACGGGCGGC CGCTATAACC CGGGCGGCAT T                           101
```

( 2 ) INFORMATION FOR SEQ ID NO:5:

( i ) SEQUENCE CHARACTERISTICS:
( A ) LENGTH: 101 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:5:

```
CTTGTCGTAA TCCGCCAGAT CCGGTTAACG GCATGGTGCA TGTGATCAAA GGCATCCAGT        60
TCGGTTCCCA AATTAAATAT TCTTGTACTA AAGGTTACCG T                           101
```

( 2 ) INFORMATION FOR SEQ ID NO:6:

( i ) SEQUENCE CHARACTERISTICS:
( A ) LENGTH: 101 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:6:

```
CCAATCAGAC GGTAACCTTT AGTACAAGAA TATTTAATTT GGGAACCGAA CTGGATGCCT        60
TTGATCACAT GCACCATGCC GTTAACCGGA TCTGGCGGAT T                           101
```

( 2 ) INFORMATION FOR SEQ ID NO:7:

( i ) SEQUENCE CHARACTERISTICS:
( A ) LENGTH: 94 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:7:

```
CTGATTGGTT CCTCCAGCGC TACATGCATC ATCTCTGGTG ATACTGTCAT TTGGGATAAT        60
GAAACACCGA TTTGTGACCG AATTCAGTAA TAAA                                    94
```

( 2 ) INFORMATION FOR SEQ ID NO:8:

( i ) SEQUENCE CHARACTERISTICS:
( A ) LENGTH: 90 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:8:

```
AGCTTTTATT ACTGAATTCG GTCACAAATC GGTGTTTCAT TATCCCAAAT GACAGTATCA        60
CCAGAGATGA TGCATGTAGC GCTGGAGGAA                                         90
```

( 2 ) INFORMATION FOR SEQ ID NO:9:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

```
TATGCGAATT    CCGTGTGGTC    TGCCGCCGAC    CATCACCAAC    GGTGATTTCA    TCTCTACCAA        60
TCGCGAGAAT    TT                                                                        72
```

( 2 ) INFORMATION FOR SEQ ID NO:10:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

```
CATAGTGAAA    ATTCTCGCGA    TTGGTAGAGA    TGAAATCACC    GTTGGTGATG    GTCGGCGGCA        60
GACCACACGG    AATTCGCA                                                                  78
```

( 2 ) INFORMATION FOR SEQ ID NO:11:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

```
TCACTATGGT    TCTGTGGTGA    CCTACCGCTG    CAATCCGGGT    AGCGGTGGTC    GTAAGGTGTT        60
TGAGCTCGTG    GGTGAGCCGT    CCATC                                                       85
```

( 2 ) INFORMATION FOR SEQ ID NO:12:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

```
GTGCAGTAGA    TGGACGGCTC    ACCCACGAGC    TCAAACACCT    TACGACCACC    GCTACCCGGA        60
TTGCAGCGGT    AGGTCACCAC    AGAAC                                                       85
```

( 2 ) INFORMATION FOR SEQ ID NO:13:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

TACTGCACTA GTAATGACGA TCAAGTGGGC ATCTGGAGCG GCCCGGCACC GCAGTGCATC    60

ATCCCGAACA AATAATAAA    79

( 2 ) INFORMATION FOR SEQ ID NO:14:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

AGCTTTTATT ATTTGTTCGG GATGATGCAC TGCGGTGCCG GGCCGCTCCA GATGCCCACT    60

TGATCGTCAT TACTA    75

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GAGACTCATA TGCAGTGCAA CGCTCCGGAA    30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

GTCAGCAAGC TTTTATTACT GAATTCGGTC    30

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

ATCGTAACTA GTAACGACGA TCAAGTGGGC    30

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

ATGACTAAGC TTTTATTATG AGCAGCTCGG                                                                30

( 2 ) INFORMATION FOR SEQ ID NO:19:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

TAACTAGTAA CGACGATCAA GTGGGCATCT GG                                                             32

( 2 ) INFORMATION FOR SEQ ID NO:20:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

CTAAGCTTTT ATTATGAGCA GCTCGGGAGT TCC                                                            33

( 2 ) INFORMATION FOR SEQ ID NO:21:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

CTAGTAACGA CGATCAAGTG GGCATCTGGA GCGGCCCGGC ACCGCAGTGC ATCATCCGA                                 60

ACAAATGCAC GCCGCCAAAT G                                                                         81

( 2 ) INFORMATION FOR SEQ ID NO:22:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

GTTCTCCACA TTTGGCGGCG TGCATTTGTT CGGGATGATG CACTGCGGTG CCGGGCCGCT                                60

CCAGATGCCC ACTTGATCGT CGTTA                                                                     85

( 2 ) INFORMATION FOR SEQ ID NO:23:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

TGGAGAACGG TATCCTGGTA TCTGACAACC GTTCTCTGTT CTCTTTAAAC GAAGTTGTAG                                60

AGTTTCGTTG TCAGCCGGGC TTTGTTATGA                                                    90

( 2 ) INFORMATION FOR SEQ ID NO:24:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

CGGACCTTTC ATAACAAAGC CCGGCTGACA ACGAAACTCT ACAACTTCGT TTAAAGAGAA              60

CAGAGAACGG TTGTCAGATA CCAGGATACC                                                    90

( 2 ) INFORMATION FOR SEQ ID NO:25:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

AAGGTCCGCG CCGTGTGAAG TGCCAGGCCT TGAACAAATG GGAGCCGGAA CTCCCGAGCT              60

GCTCATAATA AA                                                                       72

( 2 ) INFORMATION FOR SEQ ID NO:26:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

AGCTTTTATT ATGAGCAGCT CGGGAGTTCC GGCTCCCATT TGTTCAAGGC CTGGCACTTC              60

ACACGGCG                                                                            68

( 2 ) INFORMATION FOR SEQ ID NO:27:

( i ) SEQUENCE CHARACTERISTICS:
        ( A ) LENGTH: 197 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:27:

```
Met  Gln  Cys  Asn  Ala  Pro  Glu  Trp  Leu  Pro  Phe  Ala  Arg  Pro  Thr  Asn
 1              5                        10                       15

Leu  Thr  Asp  Glu  Phe  Glu  Phe  Pro  Ile  Gly  Thr  Tyr  Leu  Asn  Tyr  Glu
               20                        25                       30

Cys  Arg  Pro  Gly  Tyr  Ser  Gly  Arg  Pro  Phe  Ser  Ile  Ile  Cys  Leu  Lys
          35                        40                       45

Asn  Ser  Val  Trp  Thr  Gly  Ala  Lys  Asp  Arg  Cys  Arg  Arg  Lys  Ser  Cys
     50                        55                       60
```

-continued

```
Arg  Asn  Pro  Pro  Asp  Pro  Val  Asn  Gly  Met  Val  His  Val  Ile  Lys  Gly
 65             70                       75                            80

Ile  Gln  Phe  Gly  Ser  Gln  Ile  Lys  Tyr  Ser  Cys  Thr  Lys  Gly  Tyr  Arg
               85                       90                            95

Leu  Ile  Gly  Ser  Ser  Ser  Ala  Thr  Cys  Ile  Ile  Ser  Gly  Asp  Thr  Val
              100                      105                           110

Ile  Trp  Asp  Asn  Glu  Thr  Pro  Ile  Cys  Asp  Arg  Ile  Pro  Cys  Gly  Leu
          115                      120                      125

Pro  Pro  Thr  Ile  Thr  Asn  Gly  Asp  Phe  Ile  Ser  Thr  Asn  Arg  Glu  Asn
     130                      135                      140

Phe  His  Tyr  Gly  Ser  Val  Val  Thr  Tyr  Arg  Cys  Asn  Pro  Gly  Ser  Gly
145                      150                      155                           160

Gly  Arg  Lys  Val  Phe  Glu  Leu  Val  Gly  Glu  Pro  Ser  Ile  Tyr  Cys  Thr
                    165                      170                           175

Ser  Asn  Asp  Asp  Gln  Val  Gly  Ile  Trp  Ser  Gly  Pro  Ala  Pro  Gln  Cys
               180                      185                      190

Ile  Ile  Pro  Asn  Lys
          195
```

( 2 ) INFORMATION FOR SEQ ID NO:28:

( i ) SEQUENCE CHARACTERISTICS:
        ( A ) LENGTH: 76 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:28:

```
Met  Arg  Ile  Pro  Cys  Gly  Leu  Pro  Pro  Thr  Ile  Thr  Asn  Gly  Asp  Phe
 1              5                       10                            15

Ile  Ser  Thr  Asn  Arg  Glu  Asn  Phe  His  Tyr  Gly  Ser  Val  Val  Thr  Tyr
               20                       25                            30

Arg  Cys  Asn  Pro  Gly  Ser  Gly  Gly  Arg  Lys  Val  Phe  Glu  Leu  Val  Gly
               35                       40                            45

Glu  Pro  Ser  Ile  Tyr  Cys  Thr  Ser  Asn  Asp  Asp  Gln  Val  Gly  Ile  Trp
     50                       55                       60

Ser  Gly  Pro  Ala  Pro  Gln  Cys  Ile  Ile  Pro  Asn  Lys
 65                       70                       75
```

( 2 ) INFORMATION FOR SEQ ID NO:29:

( i ) SEQUENCE CHARACTERISTICS:
        ( A ) LENGTH: 254 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:29:

```
Met  Gln  Cys  Asn  Ala  Pro  Glu  Trp  Leu  Pro  Phe  Ala  Arg  Pro  Thr  Asn
 1              5                       10                            15

Leu  Thr  Asp  Glu  Phe  Glu  Phe  Pro  Ile  Gly  Thr  Tyr  Leu  Asn  Tyr  Glu
               20                       25                            30

Cys  Arg  Pro  Gly  Tyr  Ser  Gly  Arg  Pro  Phe  Ser  Ile  Ile  Cys  Leu  Lys
               35                       40                            45

Asn  Ser  Val  Trp  Thr  Gly  Ala  Lys  Asp  Arg  Cys  Arg  Arg  Lys  Ser  Cys
```

|     |     |     |     | 50  |     |     |     |     | 55  |     |     |     |     | 60  |     |
| --- | --- | --- | --- | --- | --- | --- | --- | --- | --- | --- | --- | --- | --- | --- | --- |
| Arg | Asn | Pro | Pro | Asp | Pro | Val | Asn | Gly | Met | Val | His | Val | Ile | Lys | Gly |
| 65  |     |     |     |     | 70  |     |     |     |     | 75  |     |     |     |     | 80  |
| Ile | Gln | Phe | Gly | Ser | Gln | Ile | Lys | Tyr | Ser | Cys | Thr | Lys | Gly | Tyr | Arg |
|     |     |     |     | 85  |     |     |     |     | 90  |     |     |     |     | 95  |     |
| Leu | Ile | Gly | Ser | Ser | Ser | Ala | Thr | Cys | Ile | Ile | Ser | Gly | Asp | Thr | Val |
|     |     |     | 100 |     |     |     |     | 105 |     |     |     |     | 110 |     |     |
| Ile | Trp | Asp | Asn | Glu | Thr | Pro | Ile | Cys | Asp | Arg | Ile | Pro | Cys | Gly | Leu |
|     |     | 115 |     |     |     |     | 120 |     |     |     |     | 125 |     |     |     |
| Pro | Pro | Thr | Ile | Thr | Asn | Gly | Asp | Phe | Ile | Ser | Thr | Asn | Arg | Glu | Asn |
|     | 130 |     |     |     |     | 135 |     |     |     |     | 140 |     |     |     |     |
| Phe | His | Tyr | Gly | Ser | Val | Val | Thr | Tyr | Arg | Cys | Asn | Pro | Gly | Ser | Gly |
| 145 |     |     |     |     | 150 |     |     |     |     | 155 |     |     |     |     | 160 |
| Gly | Arg | Lys | Val | Phe | Glu | Leu | Val | Gly | Glu | Pro | Ser | Ile | Tyr | Cys | Thr |
|     |     |     |     | 165 |     |     |     |     | 170 |     |     |     |     | 175 |     |
| Ser | Asn | Asp | Asp | Gln | Val | Gly | Ile | Trp | Ser | Gly | Pro | Ala | Pro | Gln | Cys |
|     |     |     | 180 |     |     |     |     | 185 |     |     |     |     | 190 |     |     |
| Ile | Ile | Pro | Asn | Lys | Cys | Thr | Pro | Pro | Asn | Val | Glu | Asn | Gly | Ile | Leu |
|     |     | 195 |     |     |     |     | 200 |     |     |     |     | 205 |     |     |     |
| Val | Ser | Asp | Asn | Arg | Ser | Leu | Phe | Ser | Leu | Asn | Glu | Val | Val | Glu | Phe |
|     | 210 |     |     |     |     | 215 |     |     |     |     | 220 |     |     |     |     |
| Arg | Cys | Gln | Pro | Gly | Phe | Val | Met | Lys | Gly | Pro | Arg | Arg | Val | Lys | Cys |
| 225 |     |     |     |     | 230 |     |     |     |     | 235 |     |     |     |     | 240 |
| Gln | Ala | Leu | Asn | Lys | Trp | Glu | Pro | Glu | Leu | Pro | Ser | Cys | Ser |     |     |
|     |     |     |     | 245 |     |     |     |     | 250 |     |     |     |     |     |     |

( 2 ) INFORMATION FOR SEQ ID NO:30:

( i ) SEQUENCE CHARACTERISTICS:
        ( A ) LENGTH: 254 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:30:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Gln | Cys | Asn | Ala | Pro | Glu | Trp | Leu | Phe | Ala | Arg | Pro | Thr | Asn |     |
| 1   |     |     |     | 5   |     |     |     |     | 10  |     |     |     |     | 15  |     |
| Leu | Thr | Asp | Glu | Phe | Glu | Phe | Pro | Ile | Gly | Thr | Tyr | Leu | Asn | Tyr | Glu |
|     |     |     | 20  |     |     |     |     | 25  |     |     |     |     | 30  |     |     |
| Cys | Arg | Pro | Gly | Tyr | Ser | Gly | Arg | Pro | Phe | Ser | Ile | Ile | Cys | Leu | Lys |
|     |     | 35  |     |     |     |     | 40  |     |     |     |     | 45  |     |     |     |
| Asn | Ser | Val | Trp | Thr | Gly | Ala | Lys | Asp | Arg | Cys | Arg | Arg | Lys | Ser | Cys |
|     | 50  |     |     |     |     | 55  |     |     |     |     | 60  |     |     |     |     |
| Arg | Asn | Pro | Pro | Asp | Pro | Val | Asn | Gly | Met | Val | His | Val | Ile | Lys | Gly |
| 65  |     |     |     |     | 70  |     |     |     |     | 75  |     |     |     |     | 80  |
| Ile | Gln | Phe | Gly | Ser | Gln | Ile | Lys | Tyr | Ser | Cys | Thr | Lys | Gly | Tyr | Arg |
|     |     |     |     | 85  |     |     |     |     | 90  |     |     |     |     | 95  |     |
| Leu | Ile | Gly | Ser | Ser | Ser | Ala | Thr | Cys | Ile | Ile | Ser | Gly | Asp | Thr | Val |
|     |     |     | 100 |     |     |     |     | 105 |     |     |     |     | 110 |     |     |
| Ile | Trp | Asp | Asn | Glu | Thr | Pro | Ile | Cys | Asp | Arg | Ile | Pro | Cys | Gly | Leu |
|     |     | 115 |     |     |     |     | 120 |     |     |     |     | 125 |     |     |     |
| Pro | Pro | Thr | Ile | Thr | Asn | Gly | Asp | Phe | Ile | Ser | Thr | Asn | Arg | Glu | Asn |
|     | 130 |     |     |     |     | 135 |     |     |     |     | 140 |     |     |     |     |
| Phe | His | Tyr | Gly | Ser | Val | Val | Thr | Tyr | Arg | Cys | Asn | Pro | Gly | Ser | Gly |

```
                145                         150                         155                         160
        Gly Arg Lys Val Phe Glu Leu Val Gly Glu Pro Ser Ile Tyr Cys Thr
                        165                 170                 175

Ser Asn Asp Asp Gln Val Gly Ile Trp Ser Gly Pro Ala Pro Gln Cys
                    180              185                 190

Ile Ile Pro Asn Lys Cys Thr Pro Pro Asn Val Glu Asn Gly Ile Leu
                195                 200                 205

Val Ser Asp Asn Arg Ser Leu Phe Ser Leu Asn Glu Val Val Glu Phe
            210             215                 220

Arg Cys Gln Pro Gly Phe Val Met Lys Gly Pro His Arg Val Lys Cys
        225             230                 235                 240

Gln Ala Leu Asn Lys Trp Glu Pro Glu Leu Pro Ser Cys Ser
                        245                 250
```

( 2 ) INFORMATION FOR SEQ ID NO:31:

( i ) SEQUENCE CHARACTERISTICS:
        ( A ) LENGTH: 133 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:31:

```
        Met Arg Ile Pro Cys Gly Leu Pro Pro Thr Ile Thr Asn Gly Asp Phe
        1               5                   10                  15

Ile Ser Thr Asn Arg Glu Asn Phe His Tyr Gly Ser Val Val Thr Tyr
                    20              25                  30

Arg Cys Asn Pro Gly Ser Gly Gly Arg Lys Val Phe Glu Leu Val Gly
                35              40                  45

Glu Pro Ser Ile Tyr Cys Thr Ser Asn Asp Asp Gln Val Gly Ile Trp
            50              55                  60

Ser Gly Pro Ala Pro Gln Cys Ile Ile Pro Asn Lys Cys Thr Pro Pro
        65              70                  75                  80

Asn Val Glu Asn Gly Ile Leu Val Ser Asp Asn Arg Ser Leu Phe Ser
                        85                  90                  95

Leu Asn Glu Val Val Glu Phe Arg Cys Gln Pro Gly Phe Val Met Lys
                    100                 105                 110

Gly Pro Arg Arg Val Lys Cys Gln Ala Leu Asn Lys Trp Glu Pro Glu
                115                 120                 125

Leu Pro Ser Cys Ser
                130
```

SOLUBLE CR1 DERIVATIVES

The present invention relates to polypeptides and their use in the diagnosis and therapy of disorders involving complement activity and various inflammatory and immune disorders.

Constituting about 10% of the globulins in normal serum, the complement system is composed of many different proteins that are important in the immune system's response to foreign antigens. The complement system becomes activated when its primary components are cleaved and the products alone or with other proteins, activate additional complement proteins resulting in a proteolytic cascade. Activation of the complement system leads to a variety of responses including increased vascular permeability, chemotaxis of phagocytic cells, activation of inflammatory cells, opsonization of foreign particles, direct killing of cells and tissue damage. Activation of the complement system may be triggered by antigen-antibody complexes (the classical pathway) or, for example, by lipopolysaccharides present in cell walls of pathogenic bacteria (the alternative pathway).

Complement receptor type 1 (CR1) has been shown to be present on the membranes of erythrocytes, monocytes/macrophages, granulocytes, B cells, some T cells, splenic follicular dendritic cells, and glomerular podocytes. CR1 binds to the complement components C3b and C4b and has also been referred to as the C3b/C4b receptor. The structural organisation and primary sequence of one allotype of CR1 is known (Klickstein et al., 1987, J. Exp. Med. 165:1095–1112, Klickstein et al., 1988, J. Exp. Med. 168:1699–1717; Hourcade et al.,1988, J. Exp. Med. 168:1255–1270, WO 89/09220, WO 91/05047). It is composed of 30 short consensus repeats (SCRs) that each contain around 60–70 amino acids. In each SCR, around 29 of the average 65 amino acids are conserved. Each SCR has been proposed to form a three dimensional triple loop structure through disulphide linkages with the third and first and the fourth and second half-cystines in disulphide bonds. CR1 is further arranged as 4 long homologous repeats (LHRs) of 7 SCRs each. Following a leader sequence, the CR1 molecule consists of the N-terminal LHR-A, the next two repeats, LHR-B and LHR-C, and the most C-terminal LHR-D followed by 2 additional SCRs, a 25 residue putative transmembrane region and a 43 residue cytoplasmic tail.

Based on the mature CR1 molecule having a predicted N-terminal glutamine residue, hereinafter designated as residue 1, the first four SCR domains of LHR-A are defined herein as consisting of residues 2–58, 63–120, 125–191 and 197–252, respectively, of mature CR1.

Hourcade et al.,1988, J. Exp. Med. 168:1255–1270 observed an alternative polyadenylation site in the human CR1 transcriptional unit that was predicted to produce a secreted form of CR1. The mRNA encoded by this truncated sequence comprises the first 8.5 SCRs of CR1, and encodes a protein of about 80 kDa which was proposed to include the C4b binding domain. When a cDNA corresponding to this truncated sequence was transfected into COS cells and expressed, it demonstrated the expected C4b binding activity but did not bind to C3b (Krych et al.,1989, FASEB J. 3:A368; Krych et al. Proc. Nat Acad. Sci. 1991, 88, 4353–7). Krych et al., also observed a mRNA similar to the predicted one in several human cell lines and postulated that such a truncated soluble form of CR1 with C4b binding activity may be synthesised in humans.

In addition, Makrides et al. (1992, J. Biol. Chem. 267 (34) 24754–61) have expressed SCR 1+2 and 1+2+3+4 of LHR-A as membrane-attached proteins in CHO cells.

Several soluble fragments of CR1 have also been generated via recombinant DNA procedures by eliminating the transmembrane region from the DNAs being expressed (WO 89/09220, WO 91/05047). The soluble CR1 fragments were functionally active, bound C3b and/or C4b and demonstrated Factor I cofactor activity depending upon the regions they contained. Such constructs inhibited in vitro complement-related functions such as neutrophil oxidative burst, complement mediated hemolysis, and C3a and C5a production. A particular soluble construct, sCR1/pBSCR1c, also demonstrated in vivo activity in a reversed passive Arthus reaction (WO 89/09220, WO 91/05047; Yeh et al., 1991, J. Immunol. 146:250), suppressed post-ischemic myocardial inflammation and necrosis (WO 89/09220, WO 91/05047; Weisman et al., Science, 1990, 249:146–1511; Dupe, R. et al. Thrombosis & Haemostasis (1991) 65(6) 695.) and extended survival rates following transplantation (Pruitt & Bollinger, 1991, J. Surg. Res 50:350; Pruitt et al., 1991 Transplantation 52; 868). Furthermore, co-formulation of sCR1/pBSCR1c with p-anisoylated human plasminogen-streptokinase-activator complex (APSAC) resulted in similar anti-haemolytic activity as sCR1 alone, indicating that the combination of the complement inhibitor sCR1 with a thrombolytic agent was feasible (WO 91/05047).

Soluble polypeptides corresponding to part of CR1 have now been found to possess functional complement inhibitory, including anti-haemolytic, activity.

According to the present invention there is provided a soluble polypeptide comprising, in sequence, one to four short consensus repeats (SCR) selected from SCR 1, 2, 3 and 4 of long homologous repeat A (LHR-A) as the only structurally and functionally intact SCR domains of CR1 and including at least SCR3.

In preferred aspects, the polypeptide comprises, in sequence, SCR 1, 2, 3 and 4 of LHR-A or SCR 1, 2 and 3 of LHR-A as the only structurally and functionally intact SCR domains of CR1.

It is to be understood that variations in the amino acid sequence of the polypeptide of the invention by way of addition, deletion or conservative substitution of residues, including allelic variations, in which the biological activity of the polypeptide is retained, are encompassed by the invention. Conservative substitution is understood to mean the retention of the charge and size characteristics of the amino acid side chain, for example arginine replaced by histidine.

In one aspect, the polypeptide of the invention may be represented symbolically as follows:

$$\text{NH}_2\text{-V}^1\text{-SCR1-W}^1\text{-SCR2-X}^1\text{-SCR3-Y}^1\text{—OH} \tag{I}$$

in which SCR1 represents residues 2–58 of mature CR1, SCR2 represents residues 63–120 of mature CR1, SCR3 represents residues 125–191 of mature CR1, and $V^1$, $W^1$, $X^1$ and $Y^1$ represent bonds or short linking sequences of amino acids, preferably 1 to 5 residues in length and which are preferably derived from native interdomain sequences in CR1.

In a preferred embodiment of formula (I), $W^1$, $X^1$ and $Y^1$ represent residues 59–62, 121–124 and 192–196, respectively, of mature CR1 and $V^1$ represents residue 1 of mature CR1 optionally linked via its N-terminus to methionine.

In another aspect the polypeptide of the invention may be represented symbolically as follows:

$$\text{NH}_2\text{-V}^2\text{-SCR1-W}^2\text{-SCR2-X}^2\text{-SCR3-Y}^2\text{-SCR4-Z}^2\text{OH} \tag{II}$$

in which SCR1, SCR2 and SCR3 are as hereinbefore defined, SCR4 represents residues 197-252 of mature CR1 and $V^2$, $W^2$, $X^2$, $Y^2$ and $Z^2$ represents bonds or short linking sequences of amino acids, preferably 1 to 5 residues in length and which are preferably derived from native interdomain sequences in CR1.

In preferred embodiments of formula (II), $W^2$, $X^2$, $Y^2$ and $Z^2$ represent residues 59–62, 121–124, 192–196, and residues 253 respectively, of mature CR1 and $V^2$ represents residue 1 of mature CR1 optionally linked via its N-terminus to methionine.

In one particular embodiment of formula (II) arginine 235 is replaced by histidine.

In the preferred embodiment of formula (II), residue 235 is arginine.

In one further aspect, the polypeptide of the invention may be represented symbolically as follows:

$$\text{NH}_2\text{-}X^3\text{-SCR3-}Y^3\text{—OH} \qquad\qquad\qquad (III)$$

in which SCR3 is as hereinbefore defined and $X^3$ and $Y^3$ represent bonds or short linking sequences of amino acids, preferably 1 to 5 residues in length and which are preferably derived from native interdomain sequences in CR1.

In a preferred embodiment of formula (III) $X^3$ represents amino acids 122–124 of mature CR1 optionally linked to methionine at its N-terminus and $Y^4$ represents amino acids 192–196 of mature CR1.

In another further aspect, the polypeptide of the invention may be represented symbolically as follows:

$$\text{NH}_2\text{-}X^4\text{-SCR3-}Y^4\text{-SCR4-}Z^4\text{—OH} \qquad\qquad (IV)$$

in which SCR3 and SCR4 are as hereinbefore defined and $X^4$, $Y^4$ and $Z^4$ represent bonds or short linking sequences of amino acids, preferably 1 to 5 residues in length and which are preferably derived from native interdomain sequences in CR1.

In a preferred embodiment of formula (IV) $X^4$ represents amino acids 122–124 of mature CR1 optionally linked to methionine at its N-terminus and $Y^4$ and $Z^4$ represent amino acids 192–196 and 253 respectively of mature CR1.

In a further aspect, the invention provides a process for preparing a CR1 polypeptide according to the invention which process comprises expressing DNA encoding said polypeptide in a recombinant host cell and recovering the product.

In particular, the process may comprise the steps of:

i) preparing a replicable expression vector capable, in a host cell, of expressing a DNA polymer comprising a nucleotide sequence that encodes said polypeptide;

ii) transforming a host cell with said vector;

iii) culturing said transformed host cell under conditions permitting expression of said DNA polymer to produce said polypeptide; and iv) recovering said polypeptide.

The DNA polymer comprising a nucleotide sequence that encodes the polypeptide also forms part of the invention.

The process of the invention may be performed by conventional recombinant techniques such as described in Sambrook et al., Molecular Cloning: A laboratory manual 2nd Edition. Cold Spring Harbor Laboratory Press (1989) and DNA Cloning vols I, II and III (D. M. Glover ed. IRL Press Ltd).

The invention also provides a process for preparing the DNA polymer by the condensation of appropriate mono-, di- or oligomeric nucleotide units.

The preparation may be carried out chemically, enzymatically, or by a combination of the two methods, in vitro or in vivo as appropriate. Thus, the DNA polymer may be prepared by the enzymatic ligation of appropriate DNA fragments, by conventional methods such as those described by D. M. Roberts et al., in Biochemistry 1985, 24, 5090–5098.

The DNA fragments may be obtained by digestion of DNA containing the required sequences of nucleotides with appropriate restriction enzymes, by chemical synthesis, by enzymatic polymerisation, or by a combination of these methods.

Digestion with restriction enzymes may be performed in an appropriate buffer at a temperature of 20°–70° C., generally in a volume of 50 μl or less with 0.1–10 μg DNA.

Enzymatic polymerisation of DNA may be carried out in vitro using a DNA polymerase such as DNA polymerase 1 (Klenow fragment) in an appropriate buffer containing the nucleoside triphosphates dATP, dCTP, dGTP and dTTP as required at a temperature of 10°–37° C., generally in a volume of 50 μl or less.

Enzymatic ligation of DNA fragments may be carried out using a DNA ligase such as T4 DNA ligase in an appropriate buffer at a temperature of 4° C. to 37° C., generally in a volume of 50 μl or less.

The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie, Weinheim (1982), or in other scientific publications, for example M. J. Gait, H. W. D. Matthes M. Singh, B. S. Sproat and R. C. Titmas, Nucleic Acids Research, 1982, 10, 6243; B. S. Sproat and W. Bannwarth, Tetrahedron Letters, 1983, 24, 5771; M. D. Matteucci and M. H. Caruthers, Tetrahedron Letters, 1980, 21, 719; M. D. Matteucci and M. H. Caruthers, Journal of the American Chemical Society, 1981, 103, 3185; S. P. Adams et al., Journal of the American Chemical Society, 1983, 105, 661; N. D. Sinha, J. Biernat, J. McMannus and H. Koester, Nucleic Acids Research, 1984, 12, 4539; and H. W. D. Matthes et al., EMBO Journal, 1984, 3, 801. Preferably an automated DNA synthesiser (for example, Applied Biosystems 381A Synthesiser) is employed.

The DNA polymer is preferably prepared by ligating two or more DNA molecules which together comprise a DNA sequence encoding the polypeptide.

The DNA molecules may be obtained by the digestion with suitable restriction enzymes of vectors carrying the required coding sequences.

The precise structure of the DNA molecules and the way in which they are obtained depends upon the structure of the desired product. The design of a suitable strategy for the construction of the DNA molecule coding for the polypeptide is a routine matter for the skilled worker in the art.

In particular, consideration may be given to the codon usage of the particular host cell. The codons may be optimised for high level expression in *E. coli* using the principles set out in Devereux et al., (1984) Nucl. Acid Res., 12, 387.

The expression of the DNA polymer encoding the polypeptide in a recombinant host cell may be carried out by means of a replicable expression vector capable, in the host cell, of expressing the DNA polymer. The expression vector is novel and also forms part of the invention.

The replicable expression vector may be prepared in accordance with the invention, by cleaving a vector compatible with the host cell to provide a linear DNA segment having an intact replicon, and combining said linear segment with one or more DNA molecules which, together with said linear segment, encode the polypeptide, under ligating conditions.

The ligation of the linear segment and more than one DNA molecule may be carried out simultaneously or sequentially as desired.

Thus, the DNA polymer may be preformed or formed during the construction of the vector, as desired. The choice of vector will be determined in part by the host cell, which may be prokaryotic, such as E. coli, or eukaryotic, such as mouse C127, mouse myeloma, chinese hamster ovary, fungi e.g. filamentous fungi or unicellular 'yeast' or an insect cell such as Drosophila. The host cell may also be in a transgenic animal. Suitable vectors include plasmids, bacteriophages, cosmids and recombinant viruses derived from, for example, baculoviruses or vaccinia.

The DNA polymer may be assembled into vectors designed for isolation of stable transformed mammalian cell lines expressing the fragment e.g. bovine papillomavirus vectors in mouse C127 cells, or amplified vectors in chinese hamster ovary cells (DNA Cloning Vol. II D. M. Glover ed. IRL Press 1985; Kaufman, R. J. et al. Molecular and Cellular Biology 5, 1750–1759, 198J; Pavlakis G. N. and Hamer, D. H. Proceedings of the National Academy of Sciences (USA) 80, 397–401, 1983; Goeddel, D. V. et al., European Patent Application No. 0093619, 1983).

The preparation of the replicable expression vector may be carried out conventionally with appropriate enzymes for restriction, polymerisation and ligation of the DNA, by procedures described in, for example, Sambrook et al. cited above. Polymerisation and ligation may be performed as described above for the preparation of the DNA polymer. Digestion with restriction enzymes may be performed in an appropriate buffer at a temperature of 20°–70° C., generally in a volume of 50 μl or less with 0.1–10 μg DNA.

The recombinant host cell is prepared, in accordance with the invention, by transforming a host cell with a replicable expression vector of the invention under transforming conditions. Suitable transforming conditions are conventional and are described in, for example, Sambrook et al., cited above, or "DNA Cloning" Vol. II, D. M. Glover ed., IRL Press Ltd, 1985.

The choice of transforming conditions is determined by the host cell. Thus, a bacterial host such as E.coli, may be treated with a solution of $CaCl_2$ (Cohen et al., Proc. Nat. Acad. Sci., 1973, 69, 2110) or with a solution comprising a mixture of RbCl, $MnCl_2$, potassium acetate and glycerol, and then with 3-[N-morpholino]-propane-sulphonic acid, RbCl and glycerol or by electroporation as for example described by Bio-Rad Laboratories, Richmond, Calif., USA, manufacturers of an electroporator. Mammalian cells in culture may be transformed by calcium co-precipitation of the vector DNA onto the cells or by using cationic liposomes.

The invention also extends to a host cell transformed with a replicable expression vector of the invention.

Culturing the transformed host cell under conditions permitting expression of the DNA polymer is carried out conventionally, as described in, for example, Sambrook et al., and "DNA Cloning" cited above. Thus, preferably the cell is supplied with nutrient and cultured at a temperature below 45° C.

The protein product is recovered by conventional methods according to the host cell. Thus, where the host cell is bacterial such as E. coli and the protein is expressed intracellularly, it may be lysed physically, chemically or enzymatically and the protein product isolated from the resulting lysate. Where the host cell is mammalian, the product is usually isolated from the nutrient medium.

Where the host cell is bacterial, such as E. coli, the product obtained from the culture may require folding for optimum functional activity. This is most likely if the protein is expressed as inclusion bodies. There are a number of aspects of the isolation and folding process that are regarded as important. In particular, the polypeptide is preferably partially purified before folding, in order to minimise formation of aggregates with contaminating proteins and minimise misfolding of the polypeptide. Thus, the removal of contaminating E. coli proteins by specifically isolating the inclusion bodies and the subsequent additional purification prior to folding are important aspects of the procedure.

The folding process is carried out in such a way as to minimise aggregation of intermediate-folded states of the polypeptide. Thus, careful consideration needs to be given to, among others, the salt type and concentration, temperature, protein concentration, redox buffer concentrations and duration of folding. The exact condition for any given polypeptide generally cannot be predicted and must be determined by experiment.

There are numerous methods available for the folding of proteins from inclusion bodies and these are known to the skilled worker in this field. The methods generally involve breaking all the disulphide bonds in the inclusion body, for example with 50 mM 2-mercaptoethanol, in the presence of a high concentration of denaturant such as 8M urea or 6M guanidine hydrochloride. The next step is to remove these agents to allow folding of the proteins to occur. Formation of the disulphide bridges requires an oxidising environment and this may be provided in a number of ways, for example by air, or by incorporating a suitable redox system, for example a mixture of reduced and oxidised glutathione.

Preferably, the inclusion body is solubilised using 8M urea, in the presence of mercaptoethanol, and protein is folded, after initial removal of contaminating proteins, by addition of cold buffer. A preferred buffer is 20 mM ethanolamine containing 1 mM reduced glutathione and 0.5 mM oxidised glutathione. The folding is preferably carried out at a temperature in the range 1° to 5° C. over a period of 1 to 4 days.

If any precipitation or aggregation is observed, the aggregated protein can be removed in a number of ways, for example by centrifugation or by treatment with precipitants such as ammonium sulphate. Where either of these procedures are adopted, monomeric polypeptide is the major soluble product.

If the bacterial cell secretes the protein, folding is not usually necessary.

The polypeptide of this invention is useful in the treatment or diagnosis of many complement-mediated or complement-related diseases and disorders including, but not limited to, those listed below.

Disease and Disorders Involving Complement Neurological Disorders multiple sclerosis stroke Guillain Barré Syndrome traumatic brain injury Parkinson's disease allergic encephalitis Alzheimer's disease Disorders of Inappropriate or Undesirable Complement Activation haemodialysis complications
hyperacute allograft rejection
xenograft rejection
corneal graft rejection
interleukin-2 induced toxicity during IL-2 therapy
paroxysmal nocturnal haemoglobinuria
Inflammatory Disorders
    inflammation of autoimmune diseases
    Crohn's Disease
    adult respiratory distress syndrome
    thermal injury including burns or frostbite
    uveitis
    psoriasis
    asthma
    acute pancreatitis
Post-Ischemic Reperfusion Conditions
    myocardial infarction
    balloon angioplasty
    atherosclerosis (cholesterol-induced) & restenosis
    hypertension
    post-pump syndrome in cardiopulmonary bypass or renal haemodialysis
    renal ischemia
    intestinal ischaemia
Infectious Diseases or Sepsis
    multiple organ failure
    septic shock
Immune Complex Disorders and Autoimmune Diseases
    rheumatoid arthritis
    systemic lupus erythematosus (SLE)
    SLE nephritis
    proliferative nephritis
    glomerulonephritis
    haemolytic anemia
    myasthenia gravis
Reproductive Disorders
    antibody—or complement-mediated infertility
Wound Healing The present invention is also directed to a pharmaceutical composition comprising a therapeutically effective amount of a polypeptide, as above, and a pharmaceutically acceptable carrier or excipient.

The present invention also provides a method of treating a disease or disorder associated with inflammation or inappropriate complement activation comprising administering to a subject in need of such treatment a therapeutically effective amount of a polypeptide of this invention.

In the above methods, the subject is preferably a human.

An effective amount of the polypeptide for the treatment of a disease or disorder is the dose range of 0.01–100 mg/kg; preferably 0.1 mg–10 mg/kg.

For administration, the polypeptide should be formulated into an appropriate pharmaceutical or therapeutic composition. Such a composition typically contains a therapeutically active amount of the polypeptide and a pharmaceutically acceptable excipient or carrier such as saline, buffered saline, dextrose, or water. Compositions may also comprise specific stabilising agents such as sugars, including mannose and mannitol, and local anaesthetics for injectable compositions, including, for example, lidocaine.

Further provided is the use of a polypeptide of this invention in the manufacture of a medicament for the treatment of a disease or disorder associated with inflammation or inappropriate complement activation.

In order to inhibit complement activation and, at the same time, provide thrombolytic therapy, the present invention provides compositions which further comprise a therapeutically active amount of a thrombolytic agent. An effective amount of a thrombolytic agent is in the dose range of 0.0–10 mg/kg; preferably 0.1–5 mg/kg. Preferred thrombolytic agents include, but are not limited to, streptokinase, human tissue type plasminogen activator and urokinase molecules and derivatives, fragments or conjugates thereof. The thrombolytic agents may comprise one or more chains that may be fused or reversibly linked to other agents to form hybrid molecules (EP-A-0297882 and EP 155387), such as, for example, urokinase linked to plasmin (EP-A-0152736), a fibrinolytic enzyme linked to a water-soluble polymer (EP-A-0183503). The thrombolytic agents may also comprise muteins of plasminogen activators (EP-A-0207589). In a preferred embodiment, the thrombolytic agent may comprise a reversibly blocked in vitro fibrinolytic enzyme as described in U.S. Pat. No. 4,285,932. A most preferred enzyme is a p-anisoyl plasminogen-streptokinase activator complex as described in U.S. Pat. No. 4,808,405, and marketed by SmithKline Beecham Pharmaceuticals under the Trademark EMINASE (generic name anistreplase, also referred to as APSAC; Monk et al.,1987, Drugs 34:25–49).

Routes of administration for the individual or combined therapeutic compositions of the present invention include standard routes, such as, for example, intravenous infusion or bolus injection. Active complement inhibitors and thrombolytic agents may be administered together or sequentially, in any order.

The present invention also provides a method for treating a thrombotic condition, in particular acute myocardial infarction, in a human or non-human animal. This method comprises administering to a human or animal in need of this treatment an effective amount of a polypeptide according to this invention and an effective amount of a thrombolytic agent.

Also provided is the use of a polypeptide of this invention and a thrombolytic agent in the manufacture of a medicament for the treatment of a thrombotic condition in a human or animal. Such methods and uses may be carried out as described in WO 91/05047.

This invention further provides a method for treating adult respiratory distress syndrome (ARDS) in a human or non-human animal. This method comprises administering to the patient an effective amount of a polypeptide according to this invention.

The invention also provides a method of delaying hyperacute allograft or hyperacute xenograft rejection in a human or non-human animal which receives a transplant by administering an effective amount of a polypeptide according to this invention. Such administration may be to the patient or by application to the transplant prior to implantation.

The invention yet further provides a method of treating wounds in a human or non-human animal by administering by either topical or parenteral e.g. intravenous routes, an effective amount of a polypeptide according to this invention.

GENERAL METHODS USED IN EXAMPLES (i) DNA cleavage

Cleavage of DNA by restriction endonucleases was carried out according to the manufacturer's instructions using supplied buffers. Double digests were carried out simultaneously if the buffer conditions were suitable for both enzymes. Otherwise double digests were carried out sequentially where enzyme requiring the lowest salt concentration was added first to the digest. Once that digest was complete the salt concentration was altered and the second enzyme added.

(ii) Production of blunt ended DNA fragments

The recessed 3' termini of DNA fragments were filled in using the Klenow fragment of DNA polymerase I as described in Sambrook et al (1989).

(iii) DNA purification/ concentration and analysis

Removal of protein contaminants, nucleosides was with phenol/$CHCl_3$ followed by precipitation with ethanol. DNA was analysed on horizontal agarose gel electrophoresis: both methods are described in Sambrook et al (1989).

(iv) DNA fragment isolation

1. DNA purification on DEAE NA45 membranes

DNA fragments were purified from agarose gels by making an incision in the agarose above and just below the required DNA fragment. NA45 membranes from Schleicher & Schuell (Andermnan, Great Britain) that had been soaked in TE (10 mM Tris pH 8.0, 1 mM EDTA) were inserted into the incisions and current reapplied to the gel until the DNA fragment was trapped on the lower membrane; higher molecular weight DNA was trapped on the upper membrane. The lower membrane was removed from the gel and the DNA eluted into 0.05M arginine/1M NaCl at 70° C. for 2 hours. The DNA was then concentrated by ethanol precipitation as described in Sambrook et al (1989).

2. Electroelution

DNA fragments were excised from agarose gels and DNA extracted by electroelution using the Unidirectional Electroeluter (IBI Ltd., Cambridge, England) according to the manufacturer's instructions.

3. Gel purification

DNA fragments were excised from agarose gels and DNA extracted using the QIAEX gel extraction kit according to the manufacturers instructions (QIAGEN Inc., USA).

(v) Plasmid preparation

Large scale plasmid preparation of plasmid DNA was carried out using CsCl as described in Sambrook et al (1989) or using MAGIC MAXIPREPS® (Promega Corporation, Madison, USA) according to the manufacturers instructions. Mini-plasmid preparations were carried out using either the alkaline lysis method described in Sambrook et al (1989) or MAGIC MINIPREPS® (Promega Corporation, Madison, USA) according to the manufacturer's instructions.

(vi) Introduction of plasmid DNA into *E. coli*

1. Plasmids were transformed into *E. coli* HB101 or *E. coli* BL21 (DE3) (Studier and Moffat, 1986) that had been made competent using calcium chloride as described in Sambrook et al (1989).

2. Alternatively plasmids were introduced into *E.coli* DH1 (Low,1968) or *E.coli* BL21 (DE3) by electroporation using the GENE PULSAR® and PULSE CONTROLLER® of Bio-Rad (Bio-Rad Laboratories, Richmond, Calif., USA) according to the manufacturer's instructions.

(vii) Kinasing of oligonucleotides

Oligonucleotides or annealed oligonucleotides possessing 5' overhangs were kinased using $T_4$ polynucleotide kinase as described in Sambrook et al (1989).

(viii) Annealing and ligation of oligonucleotides

Oligonucleotides were annealed together by mixing generally equimolar concentrations of the complementary oligonucleotides in 10 mM Tris pH 8.5, 5 mM $MgCl_2$ and placing at 100° C. for 5 minutes and then cooling very slowly to room temperature. Annealed oligonucleotides with sticky ends were ligated to vector or other oligonucleotides containing complementary sticky ends using $T_4$ DNA ligase as described in Sambrook et al (1989).

(ix) PCR (Polymerase Chain Reaction) amplification of DNA

DNA fragments from ligation reactions or DNA fragments excised and purified from agarose gels were amplified by PCR from two primers complementary to the 5' ends of the DNA fragment. Approximately 0.1–1 μg of ligation reaction or the purified DNA from the agarose gel was mixed in 10 mM Tris pH 8.3 (at 25° C.), 50 mM KCl;, 0.1% gelatin; $MgCl_2$ concentrations were varied from 1.5 mM to 6 mM to find a suitable concentration for each reaction. Both primers were added to a final concentration of 2 μM; each dNTP was added to a final concentration of 0.2 mM. The final reaction volume was either 75 μl or 100 μl, which was overlayed with mineral oil to prevent evaporation. Thermal cycling was then started on a thermal cycler eg. HYBAID THERMAL REACTOR®, and a typical example of conditions used was 94° C. 7 mins, 45° C. 2 mins, hold at 45° C. for less than 5 min., and then add 5 units of Taq DNA polymerase (purchased from a commercial source, e.g. Gibco). The DNA fragment was amplified by cycling the temperature at 72° C. 2 mins, 94° C. 1 min and 45° C. 2 min a total of 35 times.

(x) DNA sequencing using the double stranded method

Sequencing was carried out using "Sequenase™" (United States Biochemical Corporation) essentially as described in the manufacturer's instructions.

(xi) DNA sequence analysis and manipulation

Analysis of sequences were carried out on a digital VAX computer using the GCG package of programmes as described in Devereux et al (1984).

(xii) Production of oligonucleotides

1. Oligonucleotides were synthesised using a GENE ASSEMBLER PLUS (Pharmacia LKB Biotechnology, Milton Keynes, England) or a 381A Synthesiser (Applied BioSystems) according to the manufacturer's instructions.

2. Oligonucleotide purification was carried out either using MONOQ® as recommended by Pharmacia or by UV shadowing where recovery of synthetic oligonucleotides was by electrophoresis through a denaturing polyacrylamide gel. The oligonucleotides were loaded onto a 12% acrylamide/7M urea gel and run at 1500V until the oligonucleotide had migrated approximately two thirds of the length of the gel. The DNA was visualised using a hand-held, long-wavelength ultraviolet lamp; and the DNA bands excised. The oligonucleotide was recovered using Sep-Pak C18 reverse phase columns (Waters) as described in Sambrook et al (1989).

(xiii) Sodium dodecyl sulphate polyacrylamide gel electrophoresis (SDS PAGE)

SDS PAGE was carried out generally using the Novex system (British Biotechnology) according to the manufacturer's instructions. Prepacked gels of acrylamide concentrations 14%, 16%, 4–20% or 10–27% were the ones most frequently used. Samples for electrophoresis, including protein molecular weight standards (LMW Kit, Pharmacia) were usually diluted in 1%(w/v)SDS—containing buffer (with or without 5%(v/v) 2-mercaptoethanol), and left at room temperature for about 0.5 to 1 h before application to the gel.

(xiv) Alteration of codon usage

The non random use of synonymous codons has been demonstrated in *E. coli* and there is some evidence to support the belief that protein production from genes containing non-optimal or minor codons (particularly at the 5' end of the gene) is less efficient than that from genes with no such codons (e.g. Chen an Inouye, 1990). A codon usage table compiled from genes highly expressed in E. coli (supplied as part of the GCG sequence analysis software package, Devereux et al, (1984)) was used to determine the optimal codons for expression in E. coli. All of the first 30 codons of all constructs (where compatible with restriction enzyme sites) were optimised for high level expression. The codons for the seven amino acids: arg, gly, ile, leu, pro, ser, ala were optimised (where compatible with restriction enzyme sites) throughout the coding sequence.

(xv) Construction of vector pBROC413

The plasmid pT7-7 (Tabor, 1990) contains DNA corresponding to nucleotides 2065–4362 of pBR322 and like pBR322 can be mobilized by a conjugative plasmid in the presence of a third plasmid ColK. A mobility protein encoded by ColK acts on the nic site at nucleotide 2254 of pBR322 initiating mobilization from this point. pT7-7 was digested with LspI and BglII and the protruding 5' ends filled in with the Klenow fragment of DNA Polymerase I. The plasmid DNA fragment was purified by agarose gel electrophoresis, the blunt ends ligated together and transformed into E. coli DH1 by electroporation. The resultant plasmid pBROC413 (FIG. 1) was identified by restriction enzyme analysis of plasmid DNA.

The deletion in pBROC413 from the LspI site immediately upstream of the ø10 promoter to the BglII site at nucleotide 434 of pT7-7 deletes the DNA corresponding to nucleotides 2065–2297 of pBR322. The nic site and adjacent sequences are therefore deleted making pBROC413 non mobilizable.

(xvi) Haemolytic assay

The anti-haemolytic activity of polypeptides was assessed by measuring the inhibition of complement mediated lysis of sheep erythrocytes sensitised with rabbit antibodies (obtained from Diamedix Corporation, Miami, USA). Human serum diluted 1:125 in 0.1M Hepes/0.15M NaCl pH 7.4 buffer was the source of complement and was prepared from a pool of volunteers essentially as described in (Dacie & Lewis, 1975). Briefly, blood was warmed to 37° C. for 5 minutes, the clot removed and the remaining serum clarified by centrifugation. The serum fraction was split into small aliquots and stored at −196° C. Aliquots were thawed as required and diluted in the Hepes buffer immediately before use.

Inhibition of complement-mediated lysis of sensitised sheep erythrocytes was measured using a standard haemolytic assay using a v-bottom microtitre plate format as follows.

50 $\mu$l of a range of concentrations (0.01–100 $\mu$g/ml but typically 0.05–25 $\mu$g/ml) of test protein diluted in Hepes buffer were incubated with 50 $\mu$l of the diluted serum for 15 minutes at 37° C. 100 $\mu$l of prewarmed sensitised sheep erythrocytes were added for 1 hour at 37° C. in a final reaction volume of 200 $\mu$l. Samples were spun at 300 g at 40° C. for 15 minutes before transferring 150 $\mu$l of supernatant to flat bottomed microtitre plates and determining the absorption at 410 nm, which reflects the amount of lysis in each test solution. Maximum lysis was determined by incubating serum with erythrocytes in the absence of any inhibitor from which the proportion of background lysis had been subtracted (determined by incubating erythrocytes with buffer). The background lysis by inhibitor was assessed by incubating inhibitor with erythrocytes and then subtracting that from test samples. Inhibition was expressed as a fraction of the total cell lysis such that IH50 represents the concentration of inhibitor required to give 50% inhibition of lysis.

(xvii) C3a RIA Assay

Activation of complement pathways can be followed by measuring the release of the anaphylatoxin, C3a and its breakdown product C3a des Arg. Both products can be measured using a competitive radio-immuno assay purchased from Amersham International plc, U. K., (human complement C3a des Arg [$^{125}$I]assay, code RPA 518).

(a) Alternative pathway activation by Zymosan A

The alternative pathway of complement was activated with zymosan A, a complex carbohydrate from yeast (Sigma, catalogue number Z-4250). Zymosan A was made 50 mg/ml in Hepes buffer (0.1M Hepes/0.15M NaCl pH 7.4) or in PBS (50 mM sodium phosphate/0.1M NaCl pH 7.4) and vortexed until a fine suspension had formed. Serum (prepared as described for the haemolytic assay; Method xvi) was preincubated with different concentrations of complement inhibitor diluted in Hepes buffer for 15 mins at 37° C. using the volumes given below. Zymosan A was then vortexed for a few seconds each time before addition to the samples after which samples were incubated for a further 30 mins at 37° C. The zymosan A was then spun down at approximately 11,000 g for 30 seconds at ambient temperature. Typically 100 $\mu$l of supernatant were added to an equal volume of precipitating solution provided in the kit and the subsequent supernatant assayed as described in the technical bulletin supplied by Amersham with the C3a des Arg assay RIA kit. Each sample was assayed in duplicate and useful dilutions of the supernatant, to ensure that sample counts were on the standard curve, were found to be $^{1}/_{50}$–$^{1}/_{100}$. EDTA or Futhan were not used in any solutions or tubes as suggested in the technical bulletin.

Each sample was counted for 1 minute on an LKB-Wallac 1272 CLINIGAMMA®. Data was processed using the Ria-Calc program for RIA assays as supplied with the Clinigamma. The data was computed essentially as described in the Amersham technical bulletin with the standard curve constructed by non-linear regression fit to the data.

The miniaturised assay was carried out essentially as described above but using smaller total volumes for the activation of serum.

| | Volumes of samples added | | |
|---|---|---|---|
| | serum | inhibitor | Zymosan A |
| Normal Assay | 79 $\mu$l | 20 $\mu$l | 21 $\mu$l |
| Miniaturised Assay | 26.3 $\mu$l | 6.7 $\mu$l | 7 $\mu$l |

In the niinaturised assay, after activation, typically 25 $\mu$l of the sample were precipitated. The assay kit reagent additions were reduced from 50 $\mu$l to 10 $\mu$l which enabled the assay to be carried out in a U-bottom microtitre plate containing separate detachable wells. The assay was then carried out as described in the technical bulletin using the adjusted volumes until the last dilution in isotonic saline. In this instance 200 $\mu$l of saline were added and the plate spun at approximately 2500 g for 12 mins at 4° C. The supernatants from each well were carefully removed by aspiration and the precipitate was washed with a further 300 $\mu$l of isotonic saline. The plate was then spun again at about 2500 g for 5 mins, 4° C. and the supernatant was discarded. Wells were then counted for 10 mins each on the CLINIGAMMA. The data was processed as above.

To determine the % inhibition of maximum activation at each inhibitor concentration, a number of controls were carried out with each experiment. These included maximum activation (A) i.e. serum+zymosan A only, background activation (B) i.e. serum+buffer only, and background activation in the presence of inhibitor (C) i.e. serum+inhibitor only. The background activation was generally subtracted from the maximum activation. Similarly the background activation in the presence of inhibitor was subtracted from the value of activated serum in the presence of inhibitor. These values could then be used to determine the % inhibition at each inhibitor concentration, using the following formula:

$$1 - \frac{(D-C)}{(A-B)} \times 100$$

where D is the value of activation of serum in the presence of inhibitor and zymosan A. The IC50 is defined as the concentration of inhibitor required to reduce maximum activation by 50%.

(b) Classical pathway activation by heat aggregated IgG

Activation of the classical pathway by IgG was performed as follows. Human γ-globulin (Sigma, catalogue number G-4386) was made 14 mg/ml in 0.1M Hepes/0.15M NaCl pH 7.4 and heated at 60° C. for 1 hour. Samples of heat aggregated IgG were then stored as small aliquots at −80° C. until required. Serum was activated using heat aggregated IgG using the same volumes as described for the zymosan A normal or miniaturised assay. Preincubation of inhibitor with serum was for 15 mins at 37° C. followed by addition of the heat aggregated IgG. Incubation was continued for a further 45 mins at 37° C. The samples were then assayed directly for C3a levels using either the normal or miniaturised assay.

(xviii) C5a RIA Assay

Activation of complement pathways can be followed by measuring the release of the anaphylatoxin C5a and its breakdown product C5a des Arg. Both products can be measured using a competitive radio-immuno assay purchased from Amersham International plc, U. K., (human complement C5a des Arg [$^{125}$I]assay, code RPA 520).

The alternative pathway of complement was activated with zymosan A, as described for the C3a RIA assay (Method (xvii)). The assay was carried out in the miniaturised form as described for the C3a assay using the reagents provided in the C5a des-Arg RIA kit.

References in the Examples to amino acid numbering relate to the corresponding residues of mature CR1 protein.

EXAMPLE 1

Construction of plasmid pDB1010-D11 encoding SCR 1+2 General points

A DNA sequence for SCR 1+2 corresponding to amino acid 1 and ending at amino acid 124 of mature human complement receptor 1 was designed such that the 5' end of the gene contained an NdeI site. This site comprises an ATG codon to give the initiating methionine required for the start of mRNA translation and places the gene an optimum distance from the Shine-Dalgarno ribosome binding sequence of pBROC413. The 3' end of the gene finished on two stop codons followed by a HindIII site.

Restriction endonucleases that do not cut pBROC413 and that were commercially available were identified. The sequences of the restriction sites recognised by the endonucleases were translated into all three reading frames. The sites that contained rarely used codons for *E. coli* expression were discarded. The remaining sites were matched with the DNA coding for SCR 1+2. If the restriction site could be fitted into the DNA sequence so as to preserve the coding sequence and not add a rarely used codon, the DNA sequence was altered to include this restriction site. 10 unique restriction sites were so identified and incorporated. To enable intracellular expression of protein in *E. coli*, an ATG codon was added to the 5' end of the gene immediately preceding the codon for the first amino acid of mature CR-1. The codon ATG is part of the NdeI restriction site which can be used for cloning into vectors such as pBROC413. The codon corresponding to proline 124 of mature CR-1 has been changed to one encoding glutamine, which also encompasses an EcoRI site.

(a) Construction of plasmid

Oligonucleotides coding for SCR 1+2 (Table 1; 1–8) were synthesised as 4 complementary pairs of 87–101 mers that could be ligated in a unique fashion via complementary 8 bp overhangs between the pairs of oligonucleotides. The four complementary pairs of oligonucleotides were designated Pair A (oligos 1+2), Pair B (oligos 3+4), Pair C (oligos 5+6) and Pair D (oligos 7+8). Pair A which corresponded to the 5' end of the gene contained an NdeI restriction site overhang and Pair D contained a HindIII restriction site overhang at the 3' end. All oligonucleotides apart from 1 and 2 were purified on Pharmacia Mono Q columns prior to use. Oligonucleotide 2 of pair A and oligonucleotide 7 of pair D were kinased before annealing with their unkinased complementary oligonucleotides 1 and 8 respectively. Oligonucleotides pairs B and C were annealed first and then kinased. The kinased oligonuleotide pairs were ligated Pair A (approx. 0.1 μg) to Pair B (approx. 0.2 μg) and Pair C (approx. 2 μg) to Pair D (approx. 4 μg). The ligated oligonucleotides (A+B) were in turn ligated to (C+D) to form the gene coding for SCR 1+2.

The DNA coding for SCR 1+2 was amplified by PCR using two oligonucleotides (Table 1; 15 and 16) complementary to the two strands of DNA. Both oligonucleotides contained 5' unmatched ends that contained 6 bp of random sequence followed by the sequence of either NdeI or HindIII restriction sites followed by 18 bp complementary to the gene. Following PCR, a band of approximately 400 bp was visualised on horizontal agarose gel electrophoresis, which was excised and purified on DEAE NA45 membranes. The DNA was then cut with NdeI and HindIII before ligating into pBROC413 that had been cut with the same enzymes. The vector was transformed into *E. coli* HB 101 made competent with calcium chloride. Mini-plasmid preparations were made and the plasmid DNA was analysed by digestion with NdeI and HindIII. Plasmids containing the correct sized insert, were further subjected to restriction mapping with EcoRI, HpaI, KpnI and SmaI. The plasmids that displayed the correct restriction maps were analysed by DNA sequencing of both strands across the gene coding for SCR 1+2. Plasmid pDB1010-D11 was identified as having the correct sequence across the gene coding for SCR 1+2.

EXAMPLE 2

Construction, expression, purification, folding and formulation of MQ1→K196 of CR-1 (SCR 1+2+3)

General Points

The DNA coding for SCR 1+2+3 was constructed by ligating DNA coding for SCR 1+2 (Example 1a) to DNA encoding SCR 3.

General points relating to SCR 3 are presented in Example 9.

The SCR 3 coding unit corresponding to amino acid 122 and ending at amino acid 196 of mature CR1, was designed such that 5' end of the unit contained the EcoRI site at the junction of SCR's 2 & 3 as well as an NdeI site 5' to the EcoRI site. The 3' end of the unit finished on two stop codons followed by a HindIII site. The plasmids containing the SCR 3 coding unit and the SCR 1+2 coding unit were digested with EcoRI and HindIII. The SCR 3 coding unit was isolated and inserted downstream of the SCR 1+2 coding unit in the EcoRI/HindIII-cut SCR 1+2-containing plasmid, to give a plasmid containing the SCR 1+2+3 coding unit, which corresponds to amino acids 1 to 196 of mature CR1. The addition of the SCR 3 coding unit through the EcoRI site, converts the codon corresponding to a glutamine at position 124 back to the authentic amino acid (proline) that is found in CR1.

(a) Construction of plasmid pDB1013-5-4 encoding SCR 1+2+3

Three pairs of oligonucleotides (Table 1; 9–14) encompassing the SCR3 coding sequence were synthesised. The oligonucleotides were first annealed as pairs (9, 10; 11,12; 13,14) and the middle pair kinased thus allowing the three pairs to be ligated together via 8 base pair overlapping sequences. The 5' end of this trimeric molecule was designed to be complementary to NdeI digested DNA and the 3' end to HindIII digested DNA. This enabled the trimer to be cloned into NdeI/HindIII digested pBROC413 generating pBROC435 (FIG. 2). The identity of pBROC435 was checked by restriction enzyme analysis and confirmed by DNA sequencing.

Plasmid DNA from pBROC435 and pDB1010-D11 (Example 1) were both cut with EcoRI and HindIII; the EcoRI/HindIII band of pBROC435 coding for SCR 3 was purified on an DEAE NA45 membrane as was the cut vector pDB1010-D11. The SCR 3 coding unit was then ligated into pDB1010-D11 to generate pDB1013-5 which was then transformed into calcium chloride competent *E. coli* HB101. The resulting colonies were analysed by mini-plasmid preparation of DNA followed by restriction mapping. One of the colonies, termed pDB1013-5-4 (FIG. 2), contained the SCR 1+2+3 coding unit. This plasmid was then analysed for expression of the gene product.

(b) Expression of SCR 1+2+3 pDB1013-5-4 was transformed into calcium chloride competent *E. coli* BL21(DE3) and resulting colonies analysed by restriction digestion of mini-plasmid DNA preparations. Single colonies were inoculated into universals containing 10 ml of L broth or NCYZM medium and 50 µg/ml ampicillin and allowed to grow overnight at 37° C., 220 r.p.m. The overnight cultures (typically 5 ml) were used to inoculate each of 2 L conical flasks containing 500 mls of NCYZM medium, 150 µg/nml ampicillin: cultures were grown at 37° C., 220 r.p.m. until $A_{600}$ was 0.5 absorbance units. Cultures were induced with 1 mM isopropylthio$\beta$-D-galactoside (IPTG) and allowed to grow a further 3 hours under the same conditions. The cultures were centrifuged (approx. 8000 g/10 min) and the supernatants discarded. The cell pellets were stored at −40° C. L broth was 1% (w/v) Bactotryptone, 0.5% (w/v) Bactoyeastextract, 0.5% (w/v) NaCl. NCYZM media was L-broth containing 0.1% (w/v) casamino acids and 0.2%(w/v) $MgSO_4.7H_2O$, pH 7.0.

(c) Isolation of soulubilised inclusion bodies

Frozen cell pellet of *E. coli* BL21 DE3 (pDB 1013-5-4) (1 litre culture) prepared in a similar way to that described in Example 2b. was allowed to thaw at 4° C. for 2 h and was then resuspended in 50 mM Tris/50 mM NaCl/1 mM EDTA/0.1 mM PMSF pH 8.0 (33 ml). The suspension was transferred to a 100 ml glass beaker and sonicated (Heat Systems-Ultrasonics W380; 70 Watts, 50×50% pulse, pulse time=5 sec.). The sonicate was immediately centrifuged (6000 g/4° C./10 min) and the supernatant was discarded. The pellet, containing the inclusion bodies, was resuspended in 20 mM Tris/8M urea/50 mM 2-mercaptoethanol/1 mM EDTA/0.1 mM PMSF pH 8.5 (100 ml) and left static at room temperature (approx. 23° C.) for 1 h. The resulting solution was centrifuged (approx. 2000 g at 4° C. for 10 min) to remove any material that had failed to solubilise. The supernatant of this spin was retained at −40° C. as the solubilised inclusion body product.

(d) Purification of SCR 1+2+3 from the solubilised inclusion body

A column (i.d., 16 mm; h, 10 mm) of S-Sepharose Fast Flow was prepared and connected into an FPLC (Pharmacia) system. The column was equilibrated with 20 mM Tris/8M urea/1 mM EDTA/50 mM 2-mercaptoethanol pH 8.5. 10 ml of thawed, solubilised inclusion body, prepared as described in Example 2c, was applied to the column and washed through with equilibration buffer. The column was then developed with a linear gradient to 1M NaCl (in equilibration buffer) followed by rinses with 1M NaCl and 2M NaCl (also in equilibration buffer). All the chromatography was at 1.0 ml min$^{-1}$ and at room temperature.

Analysis by SDS PAGE/protein staining of the fractions collected during the chromatography indicated that virtually all the SCR 1+2+3 polypeptide had absorbed to the column and had been dissociated by the 1M NaCl -containing buffer. The appropriate fractions were stored at −40° C.

Subsequent assay for protein content of the peak fraction using the Bradford protein assay and a bovine serum albumin standard showed it contained 2.8 mg protein.

(e) Folding

S-Sepharose-purified SCR 1+2+3 that had been purified in a similar way to that described in Example 2d and stored at −40° C. was thawed and 0.4 ml buffer-exchanged into 0.05M formic acid using Sephaex G25 (P10). The absorbance at 280 nm of the buffer-exchanged solution was determined as 0.52, and, using $\epsilon=34000$ and appropriate correction factors for dilution, the protein concentration of the original preparation (prior to buffer-exchange) was calculated to be 0.6 mg/mnl.

Based on this figure, 1.7 ml S-Sepharose-purified protein was diluted with 0.85 ml 20 mM Tris/8M urea/50 mM 2-mercaptoethanol/1M NaCl pH 8.5 to give a 0.4 mg/ml solution, on which the folding was carried out.

Folding was effected by a series of dilutions, using cold diluent at all times.

At t=0 h, 0.8 ml SCR1+2+3 (0.4 mg/ml) was added to 0.8 ml 20 mM Tris/1M urea/5 mM EDTA/3 mM 2-mercaptoethanol pH 8.0 ('diluent') in a 30 ml polystyrene universal container. The solution was mixed thoroughly by gentle swirling and left static, capped, in a cold room (approx. 2° to 3° C.).

At 1 h, 1.6 ml diluent was added and mixed.

At 2 h, 3.2 ml diluent was added and mixed.

At 4 h, 6.4 ml diluent was added and mixed.

The solution was left a further 20 h in the cold room, then ultrafiltered (YM5, Amicon Ltd) to approx. 1.4 ml. This was buffer-exchanged into 0.1M $NH_4HCO_3$ (2.5 ml) using Sephadex G25 (PD 10) in the cold room. The eluate was aliquoted and was stored at −40° C. or lyophilised.

The product containing SCR 1+2+3 was analysed by SDS PAGE, followed by protein staining. In both non-reduced and reduced (with 2-mercaptoethanol 5% (v/v)) samples there was a single major band. The molecular weight of the reduced band, compared to reduced protein standards of known $M_r$, was approx. 24,000. The non-reduced protein (band) had a slightly faster mobility than the reduced protein band).

The product was analysed in a functional haemolytic assay utilising antibody-sensitized sheep erythrocytes (Method (xvi)). The product showed concentration-dependent inhibition of the complement-mediated lysis of the erythrocytes with an IH50 around 0.4 µg/ml.

(f) Folding

Preparation, folding, processing and analysis were carried out exactly as described in Example 2e except (1) the diluent for the folding was 20 mM ethanolamine (pH 10.0)

(2) the folded solution was ultrafiltered to a final volume of 1.55 ml, and (3) the IH50 figure was determined as about 0.6 µg/ml.

(4) the recovery of product was approx. 100 per cent.

(g) Determination of N-terminal sequence of SCR 1+2+3

1 ml samples of growing *E.coli* BL21 (DE3) containing plasmid pDB1013-5-4 were removed 3 hours post-induction with 1 mM IPFG as described in Example 2b. These samples were spun in an eppendorf centrifuge and the resultant pellets each resuspended in 200 µl of reducing buffer (100 mM Tris pH6.8/200 mM dithiothreitol/4% (w/v) SDS/2% (w/v) bromophenol blue and 20% (v/v) glycerol and boiled for 5 minutes. 25 µl samples were applied to a 14% polyacrylamide gel. When the electrophoresis was complete the proteins were transferred to a PROBLOTT® membrane (Applied Biosystems) using a Sartoblot electroblotting apparatus (Sartorius) at 0.8 mA/cm$^2$ for 1 hour 40 mins using CAPS (3-[cyclohexylamino]- 1-propanesulphonic acid) transfer buffer. After transfer the ProBlott® membrane was stained (0.1% (w/v) Coomassie Blue R-250/40% (v/v) methanol/1% v/v acetic acid) for 20 seconds and destained using 50% (v/v) methanol. A band corresponding to a $M_r$ approx 23,000 protein was excised and the N-terminal sequence determined using a Blott cartridge in an Applied Biosystems 477A Protein Sequencer.

The sequence of the first 20 amino acids was found to agree with the predicted sequence except that residue 3 could not be identified by the sequencing protocol used.

EXAMPLE 3

Expression and purification of SCR 1+2+3 from a fermentation vessel (a) Fermentation of *E. coli* harbouring the plasmid pDB1013-5-4

*E coli* BL21 (DE3): pDB1013-5-4 was recovered from storage in liquid nitrogen by thawing a vial containing 1 ml of the culture and this was used to inoculate 100 ml of seed medium (NCYZM) containing ampicillin at 75 µg/ml. The primary and secondary seed stage fermentations were carried out in plain 500 ml shake flasks batched with 100 ml aliquots of NCYZM medium. The primary and secondary seed fermentation conditions were as follows: 37° C., 230 rpm on an orbital shaker with a 50 mm throw. The primary seed incubation time was 2 hours. The primary seed culture was used to inoculate secondary seed fermentation medium at 0.1% (v/v). The secondary seed was incubated for 14.5 hours.

Two 15 litre Biolafitte fermenters were each batched with 10 litres of NCYZM medium and 0.01% (v/v) Dow Coming DC1510 antifoam. The vessels plus media were sterilised using steam to 121° C. for 45 minutes. Ampicillin sterilised by microfiltration (0.2 µm) was added aseptically to the vessel media to a final concentration of 150 µg/ml. The fermenters were inoculated at a level of 3% (v/v) from pooled secondary seed culture. The final stage incubation conditions were 37° C., agitator 400 rpm, airflow 5 l/min (0.5 vvm). The final stage fermentations were sampled aseptically pre-inoculation, at 0 hours and thence every half hour. The samples were monitored for increases in optical density (600 nm). When the OD600 was ≧0.5, IPTG was added to give a final concentration of 1 mM. The fermentations were incubated for a further 3 hours.

The cells were recovered by centrifugation using 7000 g for 25 minutes. The total cell yield (wet weight) was 49.8 grammes.

(b) Inclusion body isolation

Inclusion bodies from 23 g (wet weight) cell pellet were isolated and solubilised essentially as described in Example 2.

(c) Purification of denatured SCR 1+2+3

The volume of solubilised inclusion body from Example 3b was approx. 800 ml. To this viscous solution was added SP-Sepharose FF (100 ml gel bed, water washed and suction dried). The mixture was swirled vigorously and left static for 1 h at room temperature. The supernatant was decanted and stored at −40° C. The remaining slurry was resuspended to a uniform suspension and poured into a glass jacket (i.d., 41.5 mm) and allowed to settle into a packed bed. This packed bed was connected into a low pressure chromatography system at 4° C. and equilibrated with 0.02M Tris/8M urea/0.05M 2-mercaptoethanol/0.001M EDTA pH 8.5. When the $A_{280}$ of the eluate had minimised, the buffer was changed (step-wise) to the equilibration buffer additionally containing 1M NaCl. A single $A_{280}$ peak was eluted, in a volume of 90 ml (equivalent to approx. 1 Vt). The solution was clear and colourless and was estimated, by $A_{280}$ determination of a buffer-exchanged sample (using an ε=25,000), to contain about 300 mg target protein. By SDS PAGE followed by protein stain the target protein was the major band present. The 90 ml product was stored at −40° C.

(d) Folding and further purification.

18 ml of the above product (nominal 60 mg) was diluted with 12 ml 0.02M Tris/8M urea/1M NaCl/0.05M 2-mercaptoethanol pH 8.5. The product (30 ml) was added as 5 ml aliquots at 1 min intervals to 930 ml freshly prepared, cold 0.02M ethanolamine/0.001M EDTA, with swirling, and left static for 1 h/4° C. Then reduced glutathione was added to 1 mM (by addition of 9.6 ml 0.1M GSH) and oxidised glutathione was added to 0.5 mM (by addition of 9.6 ml 0.05M GSSG). The solution was clear and was left static in the cold for approx. 70 h. The solution was then ultrafiltered using a YM10 membrane to a final retentate volume of about 10 ml; this retentate was cloudy. It was mixed with 90 ml 0.1M NaH$_2$PO$_4$/1M (NH$_4$)$_2$SO$_4$ pH 7.0 (Buffer A) at room temperature and then centrifuged at 4000 rpm for 20 min. The supernatant was decanted and SCR 1+2+3 protein isolated by chromatography of the supernatant on Butyl Toyopearl 650 S.

The column of Butyl Toyopearl (Vt~12 ml) was equilibrated with Buffer A. The 100 ml supernatant was applied to the column and the column washed with Buffer A. It was then developed with a linear gradient of 100% Buffer A to 100% 0.1M NaH$_2$PO$_4$ pH 7.0. All the chromatography was at room temperature at approx. 30 cmh$^{-1}$.

A major $A_{280}$ peak was eluted during the gradient. Fractions spanning the peak were analysed by SDS PAGE followed by protein stain. The most concentrated fractions of the peak contained essentially pure SCR 1+2+3 and were active in the haemolytic assay (Method (xvi)).(IH$_{50}$~0.3 µg/ml). They were stored at −40° C.

EXAMPLE 4

Formulation of Butyl Toyopearl purified SCR 1+2+3

Batches of SCR 1+2+3 that had been expressed, folded and purified in similar ways to batches described in Examples 2 and 3 and further purified by ammonium sulphate treatment and Butyl Toyopearl chromatography essentially as described in Example 3d were formulated into a useable product as follows.

Three such Butyl Toyopearl products were pooled to give a volume of about 31 ml. All 31 ml were buffer-exchanged into 0.05M formic acid (prepared using 0.2 μm-filtered 'MilliQ' water) using a column of Sephadex G25. All the chromatography was at 50 cmh$^{-1}$ at 4° C. The eluate from the column was monitored at 280 nm and the Vo fraction was collected as a single fraction. The bulk of this fraction was lyophilised in aliquots.

Analysis of the Vo pool prior to lyophilisation by both SDS PAGE/stain and C8 reverse phase HPLC showed it to be essentially pure target protein. The pool demonstrated anti-haemolytic activity (IH$_{50}$ approx. 0.3 μg/ml) and the endotoxin content was low (<1 ng/mg).

One of the lyophilised aliquots was shown to be soluble at 10 mg ml$^{-1}$ in phosphate-buffered saline and showed complement inhibitory activity in the haemolytic assay (Method xvi); the IH50 was 0.34 μg/ml.

Another of the lyophilised aliquots was examined to determine the disulphide bridge pattern. All six correct (as predicted on the basis of a consensus SCR motif) disulphides were detected.

EXAMPLE 5

Effect of SCR 1+2+3 on IgG-mediated activation of the classical pathway of complement, as measured by C3a release Inhibition of heat aggregated IgG activated serum was carried out as described in Method (xvii). Heat aggregated IgG activates the classical pathway of complement. Different concentrations (typically 4–1000 μg/ml) of inhibitor were incubated with serum in the presence of heat aggregated IgG and the % inhibition of activation at each concentration was determined. The IC50 of SCR 1+2+3 was determined as approximately 22 μg/ml indicating that SCR 1+2+3 can inhibit the classical pathway of complement.

EXAMPLE 6

Effect of SCR 1+2+3 on zymosan A-mediated activation of the alternative pathway of complement, as measured by following C3a release Inhibition of zymosan A activated serum was carried out as described in Method (xvii). Different concentrations of SCR 1+2+3 (typically in the range 1–1000 μg/ml) were incubated with serum in the presence of zymosan A and the % inhibition of activation at each concentration was determined. From several different experiments the IC50 was determined as 20–40 μg/ml indicating that SCR 1+2+3 can inhibit the alternative pathway of complement.

EXAMPLE 7

Effect of SCR 1+2+3 on zymosan A-mediated activation of the alternative pathway of complement, as measured by C5a release Inhibition of zymosan A activated serum was carried out as described in Method (xvii) and assayed as described in Method (xviii). Different concentrations of SCR 1+2+3 (typically in the range 4–700 μg/ml) were incubated with serum in the presence of zymosan A and the % inhibition of activation at each concentration was determined. From several different experiments the IC50 was determined as approximately 20–30 μg/ml, indicating that SCR 1+2+3 can inhibit the alternative pathway of complement.

EXAMPLE 8

Endotoxin content determination of purified, folded and formulated SCR 1+2+3

A batch of final product SCR 1+2+3 was prepared essentially as described in Example 4 above and was measured for endotoxin content using a method based on the gel-clot reaction of limulus amoebocyte lysate (LAL) (Atlas Bioscan Ltd.). The sensitivity of the assay was 0.125 EU/mil and this was checked by titration against a doubling dilution series prepared from standard E. coli endotoxin supplied with the LAL kit.

10-fold dilutions of ~1.3 mg/ml SCR 1+2+3 protein stock were tested in quadruplicate for their effect on LAL by adding 10 μl of sample to 10 μl LAL. After 1 h at 37° C. the mixtures were tested for either clotting or remaining liquid. (Solutions that contain at least 0.125 EU endotoxin will clot this LAL preparation.) After taking into account the results of simultaneous tests designed to test for interference, it was concluded that the endotoxin content of the SCR 1+2+3 protein preparation was <12.5 EU/ml, equivalent to approx. <1 ng/mg protein.

EXAMPLE 9

Expression, folding, purification, and formulation of MR122→K196 of CR-1 (SCR 3)

General Points

The sequence for SCR 3 corresponding to amino acid 122 and ending at amino acid 196 of mature human complement receptor 1 was designed such that the 5' end of the gene contained an NdeI restriction endonuclease site. This site comprises an ATG start codon to give the initiating methionine required for the start of MRNA translation and allows the placement of the gene an optimum distance from the Shine-Dalgarno ribosome binding site of pBROC413. This codon is followed immediately by the gene coding for SCR 3 starting with arginine 122 of mature human complement receptor 1. The 3' end of the gene finishes with a codon for lysine 196 followed by two stop codons followed by a HindIII site.

The DNA coding for SCR3 was modified for optimum codon usage in E. coli as described in the methods. The gene was also altered to incorporate unique restriction endonuclease sites. This was carried out in the following way. Restriction endonucleases that do not cut pBROC413 and were commercially available were identified. The DNA sequence of these restriction endonuclease sites was then translated into all three reading frames and the codon usage examined. Sites that contained codons that are rarely used by E. coli were discarded. The remaining sites were examined for their translated sequence and if that sequence matched with SCR 3, the restriction site was incorporated into the sequence.

(a) Construction of plasmid pBROC435 encoding SCR 3

The construction of pBROC435 is described in Example 2a (b) Expression of SCR 3 from pBROC435 pBROC435 was transformed by electroporation into E.coli BL21(DE3) and resulting colonies analysed by restriction digestion of mini-plasmid DNA preparations.

Single colonies were inoculated into universals containing 10 ml of L broth or NCYZM medium and 50–75 μg/ml ampicillin and allowed to grow overnight at 37° C., 220 r.p.m. Typically 4 ml of overnight cultures were used to inoculate each of 2 L conical flasks containing 500 ml of NCYZM medium, 150 μg/nml ampicillin; cultures were grown at 37° C., 230 r.p.m. until $A_{600}$ was 0.5 absorbance units. Cultures were induced with 1 mM IPTG and allowed to grow a further 3 hours under the same conditions. The cultures were centrifuged (approx. 8000 g/10 min) and the supernatants discarded. The cell pellets were stored at −40° C.

(c) Isolation of solubilised inclusion bodies

The frozen cell pellet of *E. coli* (from 3 l growth culture in NCYZM) described in Example 9b was allowed to thaw at room temperature for 2 h and was then resuspended in 50 mM Tris/50 mM NaCl/1 mM EDTA/0.1 mM PMSF pH 8.0 (90ml). The suspension was transferred to a 200 ml glass beaker and sonicated (Heat Systems—Ultrasonics W380; 70 Watts, 50×50% pulse, pulse time=5 sec.). The sonicate was immediately centrifuged (6000 g/4° C./10 min) and the supernatant was discarded. The pellet, containing the inclusion bodies, was resuspended in 20 mM Tris/8M urea/50 mM 2-mercaptoethanol/1 mM EDTA/0.1 mM PMSF pH 8.5 (300 ml) with gentle pipetting to mix. After mixing, the solution was left static at room temperature (approx. 23° C.) for 1 h. The resulting solution was centrifuged (2000 g at 4° C. for 10 min) to remove material that failed to solubilise. The supernatant of this spin was retained at −40° C. as the solubilised inclusion body product.

(d) Purification of SCR3 from the solubilised inclusion body

A column (i.d., 32 mm; h, 32mm) of Q-Sepharose Fast Flow (Pharmacia) was prepared and equilibrated with 20 mM Tris/8M urea/50 mM 2-mercaptoethanol pH 9.0. 200 ml of thawed, solubilised inclusion body, prepared as in Example 9c, was applied to the column and washed through with equilibration buffer. The column was connected to an FPLC system and developed via a stepwise gradient of 0.1, 1.0, 2.0M NaCl (also in equilibration buffer). All chromatography was at 2.0 ml $min^{-1}$ and at room temperature.

Analysis by SDS PAGE/protein staining of the fractions collected during the chromatography indicated that virtually all the SCR3 did not bind to the column. Many other proteins had absorbed to the column however and had been dissociated by the 0.1M and 1M NaCl—containing buffers. The purity of SCR3 in the unadsorbed fraction was estimated to be about 80%.

(e) Folding of SCR3

Q-Sepharose-purified SCR3 that had been purified as described in Example 9d and stored at −40° C. was thawed and was folded by a series of dilutions, using cold diluent. At t=0, 100 ml 20 mM Tris/1M urea/5mM EDTA/3mM 2-mercaptoethanol pH 8.0 (diluent) were added to 100 ml SCR3. At this stage the solution was turbid in appearance. The solution was mixed thoroughly by gentle swirling and left static, capped, in a cold room (2°–3° C.). At 1 h, 200 ml diluent was added and mixed, final volume=400 ml. At 2 h, 400 ml diluent was added and mixed, final volume=800 ml. At 4 h 800 ml of diluent was added and mixed, final volume=1.6 L. The solution was left for a further 20 h in the cold room. The solution now appeared clear, and it was stored at −40° C. in aliquots.

(f) Formulation of SCR3

50 ml of SCR3 prepared as in Example 9e were thawed and ultrafiltered to 3.5 ml using a 2000 Da cut-off membrane (Armicon). 2.5 ml of the concentrate was buffer-exchanged into 0.1M $NH_4HCO_3$ (3.0 ml) using Sephadex G25 (PD 10).

Subsequent analysis for protein content using the molar extinction coefficient of 11000 showed this sample contained approx 0.24 mg/ml.

Analysis of this material by SDS PAGE/protein staining indicated that the protein was about 80% pure. Samples reduced with 2-mercaptoethanol had a lower electrophoretic mobility suggesting the presence of disulphide bonds in SCR3.

Analysis of this sample in the haemolytic assay (Method (xvi)) showed it had an IR50 of approx. 10–20 μg/ml.

(g) Determination of N-terminal sequence of expressed SCR3

200μl SCR3 prepared and formulated in 0.1M $NH_4HCO_3$ as in Example 9f was precipitated with 800 μl cold acetone in a cardice/ethanol bath for 60 mins. The sample was then spun in an Eppendorf centrifuge (approx 10,000 g/20 mins) and the resultant pellet resuspended with heating in sample buffer containing 5% (v/v) 2-mercaptoethanol. 30 μl samples were electrophoresed on a 4 to 20% SDS-containing polyacrylamide gradient gel. When the electrophoresis was complete the proteins were transferred to a PROBLOTT® membrane (Applied Biosystems) using an electroblotting apparatus at 200 mA for 2 h using CAPS in 10% methanol/90%$H_2O$ (v/v)) transfer buffer. After transfer the PROBLOTT® membrane was stained (0.1%(w/v) Coomassie Blue), destained, rinsed and air dried according to the manufacturer's instructions. Sections of the membrane were excised and used for N-terminal sequencing.

The sequence of the first 20 amino acids of the major band was as expected for SCR3 with the exception of residue 5, which could not be identified.

(h) Preparation, folding and formulation of SCR3

Preparation and folding were carried out exactly as described in Example 9a–9e. 400 ml of folded SCR3 was ultrafiltered through a 30 KDa cut-off filter (Amicon) at 4° C. Samples of the ultrafiltrate were processed in two ways.

1. 50 ml were ultrafiltered using a 2 KDa cut-off membrane to a final volume of 3.5 ml and buffer-exchanged into 0.05M formic acid (6.7 ml) using Sephadex G25 (PD10) columns. The total amount of SCR3 estimated by the absorbance at 280 nm was 0.6 mg. Analysis by SDS PAGE/protein staining indicated that the protein had a purity of about 95%. The sample was freeze-dried and stored at −40° C.

2. 100ml of the ultrafiltrate were adjusted to pH 5.5 with HCl. The sample was applied to a Mono S column (1 ml) at 1.5 ml $min^{-1}$ and washed through with equilibration buffer (20 mM Tris.HCl pH 5.5). The column was then developed with a step gradient of 0.1, 1.0 and 2.0M NaCl (also in equilibration buffer). All remaining chromatography was at 1.0 ml $min^{-1}$ and at room temperature.

Analysis by SDS PAGE/protein staining of the fractions collected during the chromatography demonstrated that the major band dissociated at 1M NaCl contained SCR3 at about 95% purity.

EXAMPLE 10

Expression, folding, purification and formulation of MR122-S253 of CR-1 (SCR 3+4)

(a) Construction of plasmid pDB1019 encoding SCR 3+4

The DNA coding for SCR 3+4 was constructed from the plasmids pBROC435 (Example 2) and pDB1018-1 (Example 11) which carry the genes coding for SCR 3 and SCR 1+2+3+4 respectively. The SCR 4 coding unit was excised from pDB1018-1 and ligated onto the end of the SCR 3 coding unit in pBROC435.

pDB1018-1 was digested with SpeI and HindIII and separated on a 1% agarose gel. The band which codes for SCR 4 (~245 bp) was excised from the gel and purified using the QIAEX extraction kit. Plasmid pBROC435 was also cut with SpeI and HindIII, separated on 1% agarose, excised from the agarose and purified with the QIAEX kit. The SCR 4 coding DNA was then ligated into the cut pBROC435 plasmid to give pDB1019. This DNA was used to transform E. coli HB101 made competent with $CaCl_2$. Transformants were analysed by restriction analysis using EcoRI and HindIII. Clones carrying the correct sized insert were used for expression studies.

(b) Expression of SCR 3+4 from pDB1019-1C pDB1I019 was transformed into E. coli BL21(DE3) made competent with $CaCl_2$ and the resulting colonies were analysed by restriction digestion of mini-plasmid DNA preparations. Plasmid pDB1019-1C was identified as carrying the correct sized insert. Single colonies of E. coli BL21(DE3) carrying pDBI019-1C were inoculated into ten universals containing 10 mls of NCYZM medium and 75 μg/ml ampicillin and allowed to grow overnight at 37° C., 240 r.p.m. The overnight cultures were then used to inoculate eight 2 L conical flasks (5 ml/flask) containing 500 ml of NCYZM medium, 150 μg/ml ampicillin. Cultures were grown at 37° C., 240 r.p.m. until $A_{600}$ was 0.5 absorbance units. At this point cultures were induced with 1 mM EPTG and allowed to grow a further 3 hours under the same conditions. The cultures were centrifuged (approx. 8000 g/ 10 mins) and the supernatants were discarded. The cell pellets were stored at −40° C.

(c) Isolation, purification, folding and formulation of SCR 3+4

The methods used generally follow those described earlier for the preparation of SCR 1+2+3.

Isolation of solubilised inclusion bodies from cell pellet derived from 2 l culture was carried out as described in Example 2c. The volume of solubilisate was 200 ml.

Some of the contaminating (host) E. coli proteins were removed from the preparation by adsorption onto S-Sepharose, either in a batch process or by column chromatography, using systems similar to those described in Example 2d. The protein present in the unadsorbed fractions was shown by SDS PAGE/stain to contain significant amounts of SCR 3+4 protein. About half of these fractions were ultrafiltered using a YM1 (Amicon) membrane to approx. 35 to 40 ml. This retentate was estimated to contain about 0.3 mg protein/ml (based on $A_{280}$ determination of a buffer-exchanged sample, using $\epsilon=21,000$). 10.5 ml of the retentate was mixed with 325 ml cold 20 mM ethanolamine and left static at 4° C. for 1 hour. Then reduced glutathione was added to 1 mM (by addition of 3.4 ml 100 mM GSH) and oxidised glutathione was added to 0.5 mM (by addition of 3.4 ml 50 mM GSSG). The solution was mixed and left static at 4° C. for ~72 h. The solution was clear. The solution was then ultrafiltered using a YM1 membrane to a retentate of 5 ml. The retentate was divided in two and buffer-exchanged into either 20 mM ethanolamine or 50 mM formic acid using Sephadex G25 (PD10 columns).

Analysis of the formic acid SCR 3+4 product by reverse phase HPLC and by SDS PAGE followed by protein staining showed only one major protein species (>90% pure). The protein concentration was estimated to be 0.3 mg/ml using $A_{280}$ determinations. The product was active in the haemolytic assay (Method (xvi)); the IH50 value was approx. 30 μg/ml

EXAMPLE 11

Construction, expression, folding, purification and formulation of MQ1-S253 of CR-1 (SCR 1+2+3+4)

General points

Two constructs were prepared by making a plasimid encoding SCR 1+2, incorporating SCR3 and finally adding SCR4. The two constructs encoded consensus SCR1 to 4 and the R235H mutation of SCR1 to 4 (Example 12).

A plasmid containing the SCR 1+2+3+4 coding unit was constructed by adding the DNA encoding SCR 4 onto the construct coding for SCR 1+2+3 (Example 2). For convenience of DNA manipulation, the SCR 4 DNA coding unit was made by synthesising the DNA encoding the last 17 amino acids of SCR 3 followed by the DNA coding for the linker region followed by SCR 4. This DNA started at the SpeI site of the SCR 1+2+3 coding construct which corresponds to T175 of mature CR-1 followed by the DNA coding for the linker region followed by SCR 4 ending on the codon corresponding to S253 followed by two stop codons and a HindIII site. As for the previous constructs the DNA encoding SCR 4 was altered for optimised codon usage and restriction sites as previously described in Example 1. This unit of DNA was ligated to the plasmid coding for SCR 1+2+3 which had been cut with SpeI and HindIII to give a construct coding for SCR 1+2+3+4.

(a) Construction of plasmid pDB1018 encoding SCR 1+2+3+4

Oligonucleotides (Table 1; oligos 21–26 coding for SCR4) were synthesised as 3 complementary pairs of 68–90 mers that could be ligated in a unique fashion via complementary 8 bp overhangs between the pairs of oligonucleotides. The 3 complementary pairs of oligonucleotides were designated Pair E (oligos 21, 22), Pair F (oligos 23, 24) and Pair G (oligos 25, 26). Pair E which corresponds to the 5' end of the gene contained a SpeI restriction site overhang and Pair G contained a Hind III restriction site overhang at the 3' end. All oligonucleotides apart from 22 and 24 were purified by electrophoresis through a denaturing polyacrylamide gel followed by reverse phase chromatography ($C_{18}$). Oligonucleotides 22, 23, 24 and 25 were kinased before annealing to their complementary oligonucleotides. The oligonucleotides were ligated pair E to pair F to pair G to form the gene coding for part of SCR3 and the whole of SCR4 which for convenience will be called the SCR4 gene in the subsequent text.

The DNA coding for SCR4 was initially amplified by PCR using two oligonucleotides (Table 1; oligos 17 and 18) complementary to the two strands of DNA. Both oligonucleotides contained 5' unmatched ends that contained 6 bp of random sequence followed by the sequence of either SpeI (oligo 17) or Hind III (oligo 18) restriction sites followed by 18 bp complementary to the gene. Following PCR a band of approximately 250 bp was visualised on horizontal agarose gel electrophoresis, which was excised and purified on DEAE NA45 membranes. This DNA was used for a second PCR amplification using nested primers that had been moved inwards by four nucleotides at their 5' ends (Table 1; oligo 19, oligo 20). These oligo's incorporated the SpeI and HindIII restriction sites but now only had 2 nucleotides beyond the end of each restriction site. Following PCR a band of approx. 250 bp was visualised on horizontal agarose gel electrophoresis. This band was excised and purified using the QLIEX agarose gel extraction kit.

The DNA for SCR 4 was blunt-end ligated to itself following kinasing. The multimers formed were visualized by horizontal agarose gel electrophoresis and the bands excised and purified using the QIAEX agarose gel extraction kit. The DNA was then cut with Spe I and Hind III and ligated into pDB1013-5-4 that had been cut with the same enzymes to produce pDB1018 (FIG. 3). The vector was transforrned into E.coli HB101 made competent with calcium chloride. Mini-plasmid preparations were made and plasmid DNA analysed by digestion with Nde I, Hind III, Stu I, Spe I and Kpn I. The plasmids with the correct restriction maps were analysed by DNA sequencing of both strands across the gene encoding SCR4. Two plasmids were selected for further study. pDB1018-1, which encoded MQ1-S253 (consensus SCR1 to 4) and pDB1018-6, which encoded the R235H mutant of MQ1-S253. The amino acid sequences of the two polypeptides encoded by pDB1018-1 and pDB1018-6 are shown in Table 2.

Taking the first residue as being the A of the ATG initiating codon, DNA sequencing revealed that residue 600 of pDB 1018-6 had been altered from G→A. This is a silent mutation and does not alter the amino acid at this position.

(b) Expression of MQ1-S253 from pDB1018-1 pDB1018-1, constructed as described in Example 11a, was transformed into calcium chloride competent E.coli BL21(DE3). Single colonies were inoculated into universals containing 10 ml of NZCYM medium and 75 µg/ml ampicillin and allowed to grow overnight at 37° C., 230 r.p.m. 3ml of overnight culture were used to inoculate each of 8×2 litre conical flasks containing 500 ml of NZCYM medium, 150 µg/ml ampicillin; cultures were grown at 37° C., 230 r.p.m. until $A_{600}$ reached 0.5 absorbance units. The cultures were induced with 1 mM 1PTG and allowed to grow for a further 3 hours under the same conditions. The cultures were centrifuged (approx. 7000 g/10 mins/4° C.) and the supernatants discarded. The cell pellets were stored at −40° C.

(c) Isolation of solubilised inclusion bodies

The frozen cell pellets of E.coli BL21(DE3) (pDB1018-1) each equivalent to 1 litre of culture prepared as described in Example 11b were allowed to thaw at 0°–4° C. over 2 hours. The pellets were resuspended in 50 mM Tris/50 mM NaCl/1 mM EDTA/0.1 mM PMSF pH 8.0: 30 ml for each litre pellet. Each suspension was transferred to a 100 ml glass beaker and sonicated (Heat systems—Ultrasonics W380; 70 Watts, 50×50% pulse, pulse time=5 seconds). The sonicates were pooled and immediately centrifuged (6,000 g/4° C./10 mins) and the supernatant discarded. The pellet containing the inclusion bodies was resuspended in 20 mM Tris/8M urea/50 mM 2-mercaptoethanol/1 mM EDTA/0.1 mM PMSF pH 8.5 (400 ml), thoroughly mixed and left static at room temperature (approx. 23° C.) for 1 hour.

(d) Purification of MQ1-S253 from the solubilised inclusion body 30 ml of S-Sepharose FF that had been washed with deionised water and suction dried was added to the inclusion body solution described in Example 11c, and vigorously shaken for 30 seconds. The S-Sepharose mixture was left static at room temperature (23° C.) for 1.5 hours and then the supernatant was discarded. The remaining slurry was packed into a column (id, 4.1 cm). The column was equilibrated using 20 mM Tris/8M urea/50 mM 2-mercaptoethanol/1 mM EDTA/0.1 mM PMSF pH 8.5 at 60 cmh$^{-1}$, 4° C. MQ1-S253 protein was eluted using the equilibration buffer containing 1M NaCl. Analysis by SDS PAGE/protein staining of the fractions collected during the chromatography indicated that virtually all the target protein had adsorbed to the column and had been dissociated by the 1M NaCl wash. The appropriate fraction was stored at −40° C.

(e) Folding and formulation

Based on a molar extinction coefficient of 25,000 and $A_{280}$ values determined in 50 mM formic acid, 60 mg of the S-Sepharose purified unfolded protein described in Example 11d was folded and formulated as follows:

8.0 ml of solution (equivalent to 60 mg protein) was diluted with 22 ml cold 20 mM Tris/8M urea/50 mM 2-mercaptoethanol/1M NaCl/1 mM EDTA/0.1 mM PMSF pH8.5, to give 30 ml of a 2.0 mg/mi solution. The 30 ml was diluted rapidly with constant stirring into 930 ml cold (0°–4° C.) freshly prepared 20 mM ethanolamine. The solution was left static at 0°–4° C. for 1 hour. Reduced glutathione was added to 1 mM (by addition of 9.6 ml of 100 mM stock) and then oxidised glutathione was added to 0.5 mM (by addition of 9.6 ml of 50 mM stock). The solution was left static at 0°–4° C. for a further 48 hours and then ultrafiltered using a stirred cell (Amicon) and a YM10 membrane (Amicon, nominal 10,000 Da molecular weight cut-off) to approx. 29 ml. The ultrafiltered retentate was buffer exchanged into 50 mM formic acid using Sephadex G25 (i.d., 26 mm; h, 245 mm Vt, 123 ml) and a flow rate of 50 cmh$^{-1}$ to a final volume of 40 ml. Using a molar extinction coefficient of 25,000 for the protein 51 mg of protein was recovered. The purified protein gave an IH$_{50}$ value (see Method xvi) of approximately 2 µg/ml.

(f) Further purification and formulation of SCR1+2+3+4

Folded SCR1+2+3+4 (nominal 25mg) in 50mM formic acid prepared essentially as described in Example 11e was lyophilised. The lyophilisate was resolubilised in 20 mM ethanolamine (10 ml) to give a cloudy solution. The 10 ml were then added to 90 ml 0.1M NaH$_2$PO4/1M (NH4)$_2$SO4 pH 7.0, thoroughly mixed, and then clarified by centrifugation (4000 rpm/20 min). The supernatant (100 ml) was decanted and was chromatographed on Butyl Toyopearl (exactly as described for SCR1+2+3 in Example 3d). The peak $A_{280}$ fractions, eluting at about 100% of the 1M NaCl-containing buffer, were pooled and buffer-exchanged using Sephadex G25 into 50 mM formic acid. The Vo pool (29.5ml) was lyophilised in aliquots.

The purity of the protein was assessed by SDS PAGE followed by protein staining and by C8 reverse-phase HPLC; the protein was estimated to be >95% pure. One of the lyophilised aliquots was resolubilised to 4 mg protein/ml in 0.1M Hepes/0.15M NaCl pH7.4. The product showed activity in the haemolytic assay (Method (xvi)); the IH50 was calculated to be 0.3 µg/ml.

Another of the lyophilised aliquots was examined to determine the disulphide bridge pattern using proteolytic digestion and peptide identification by amino acid sequencing. All eight correct (as predicted on the basis of a consensus SCR motif) disulphides were detected.

EXAMPLE 12

Expression, isolation, folding and formulation of purified MQ1-S253 (R235H)

(a) Expression of MQ1-S253 (R235H)

pDB1018-6 (prepared as described in Example 11a) was transformed into calcium chloride competent E. coli BL21 (DE3). Single colonies were inoculated into universals containing 10 mls of NCYZM medium and 50 µg/ml ampicillin and allowed to grow overnight at 37° C., 220 r.p.m. The overnight cultures (approx. 3 ml) were used to inoculate each of 2 l conical flasks containing 500 ml of NCYZM medium, 150 µg/ml ampicillin; cultures were grown at 37° C., 220 r.p.m. until $A_{600}$ was 0.5 absorbance units. Cultures were induced with 1 mM IPTG and allowed to grow a further 3 hours under the same conditions. The cultures were centrifuged (approx. 8000 g/10 min/4° C.) and the supernatants discarded. The cell pellets were stored at −40° C.

(b) Isolation of solubilised inclusion bodies and purification of unfolded

MQ1-S253 (R235H)

Frozen cell pellet of E. coli BL21 DE3 (pDB 1018-6) (2 litre culture) described in Example 12a was allowed to thaw at 4° C. for 2 h and was then resuspended in 50 mM Tris/50 mM NaCl/1 mM EDTA/0.1 mM PMSF pH 8.0 (66 ml). The suspension was transferred to a 250 ml glass beaker and sonicated (Heat Systems—Ultrasonics W380; 70 Watts, 30×50% pulse time=5 seconds). The sonicate was immediately centrifuged (6000 g/4° C./10 min) and the supernatant was discarded. The pellet, containing the inclusion bodies, was resuspended by vigorous swirling in 20 mM Tris/8 M urea/50 mM 2-mercaptoethanol/1 mM EDTA/0.1 mM PMSF pH 8.5 (200 ml) and left static at room temperature (approx. 23° C.) for 1.5 h. Water-washed, suction-dried S-Sepharose (equivalent to approx. 25 ml packed bed volume) was added to the 200 ml solubilised inclusion body and the mixture swirled vigorously to wet the Sepharose beads thoroughly. The mixture was left static at room temperature for 1 h. The supernatant (approximately 150 ml) was decanted and discarded. The slurry remaining was resuspended to a uniform suspension by swirling and then poured into a 32 mm (i.d.) glass jacket and allowed to settle. The gel bed was connected into a low pressure chromatography system and was equilibrated with 20 mM Tris/8 M urea/1 mM EDTA/50 mM 2-mercaptoethanol pH 8.5 at 4° C. until the $A_{280}$ baseline stabilised. The column was then developed with equilibration buffer containing 1M NaCl. All the chromatography was at approx. 1 ml min$^{-1}$. Analysis by SDS PAGE/protein staining of the fractions collected during the chromatography indicated that most of the MQ1-S253 (R235H) polypeptide had adsorbed to the column and had been dissociated by the 1M NaCl-containing buffer wash and that the purity of the material was about 90%.

A sample of the pool was buffer-exchanged into 50 mM formic acid using Sephadex G25 column to allow some assays to be carried out.

Amino acid analysis of the pool of the MQ1-S253 (R235H)-containing fractions gave a total protein content of about 120 mg.

(c) Folding and formulation of SCR 1+2+3 (R235H)

Based on $A_{280}$ values and a molar extinction coefficient of 25,000 for the protein in 50 mM formic acid, 20 mg of the S-Sepharose-purified unfolded protein described in Example 12b was folded and formulated as follows.

5.2 ml protein solution (equivalent to 20 mg) was diluted with 4.8 ml cold 20 mM Tris/8M urea/50 mM 2-mercaptoethamol/1M NaCl pH8.5, to yield 10 ml of a 2.0 mg/ml solution.

The 10 ml was diluted rapidly with constant stirring into 310 ml freshly prepared, cold (approx. 0°–4° C.) 20 mM ethanolamine. The solution was left static at 0°–4° C. for 1 h. Then reduced glutathione was added to 1 mM (by addition of 2.56 ml 125 mM GSH). Then oxidised glutathione was added to 0.5 mM (by addition of 3.2 ml 50 mM GSSG). The solution was left static, in the cold room (~2°–3° C.), for a further 48 h. The solution was then ultrafiltered using a stirred cell and a YM10 (nominal 10,000 molecular weight out-off) membrane to approximately 2 ml. The ultrafiltration cell was washed with approximately 2 ml 20 mM ethanolamine and the wash and the ultrafiltered retentate were pooled to give a final volume of 3.7 ml.

2.2 ml of this solution was buffer-exchanged into 3.2 nml 50 mM formic acid using Sephadex G25 (PD10). The buffer-exchanged material was regarded as the product, and it was stored at −40° C. Analysis of an aliquot of the product showed it contained 1.6 mg protein/ml, that by SDS PAGE under non-reducing conditions a single major band of $M_r$~28,000 was present and that N-terminal sequencing of the band (MQXNAPE) was consistent with the expected sequence. In addition the preparation gave an $IH_{50}$ value (see Method (xvi)) of approximately 1 µg/ml.

IN THE FIGURES

FIG. 1 Plasmid pBROC413. bla indicates the ampicillin resistance gene, ø10 the T7 RNA polymerase promoter and rbs the ribosome binding site. Arrows for ø10 and bla give the direction of transcription. The polylinker site has been indicated. The plasmid is not drawn to scale and the size is approximate.

REFERENCES USED IN EXAMPLES OR GENERAL METHODS

Figure 1:
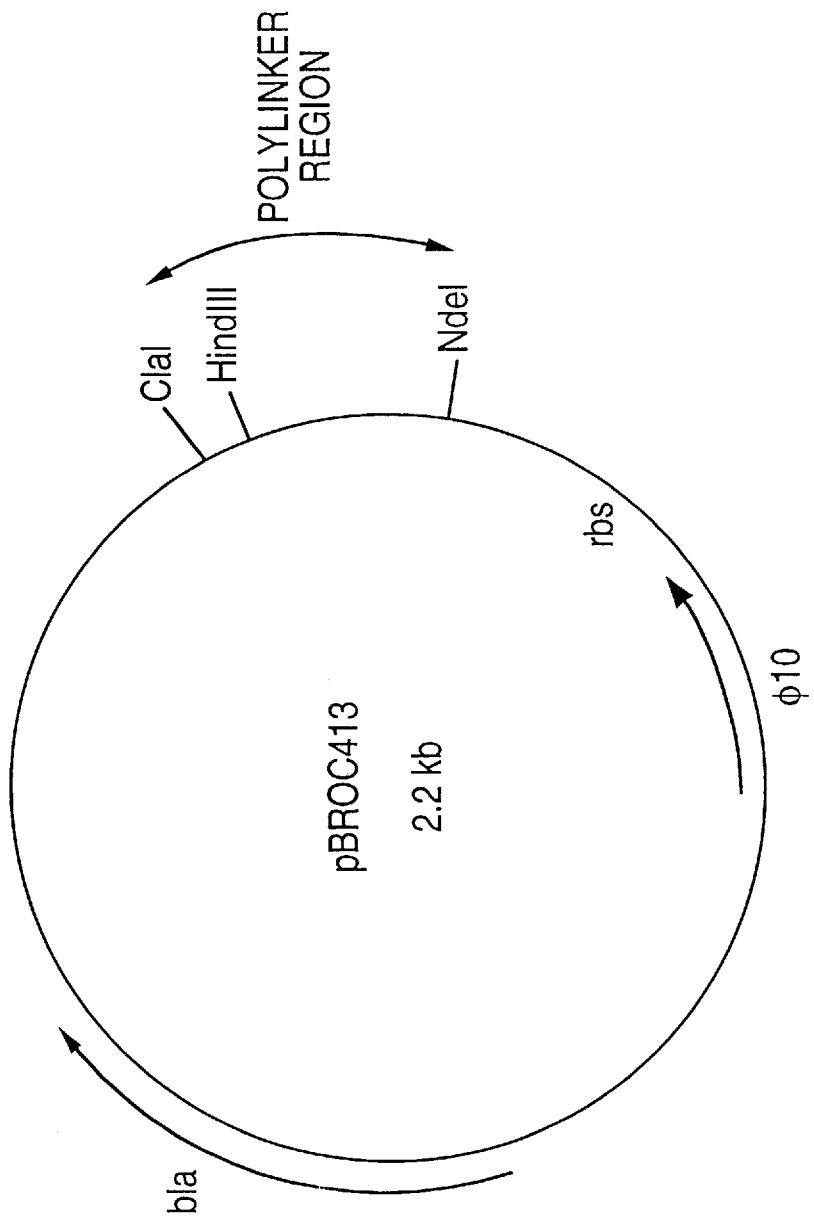
Figure 2:
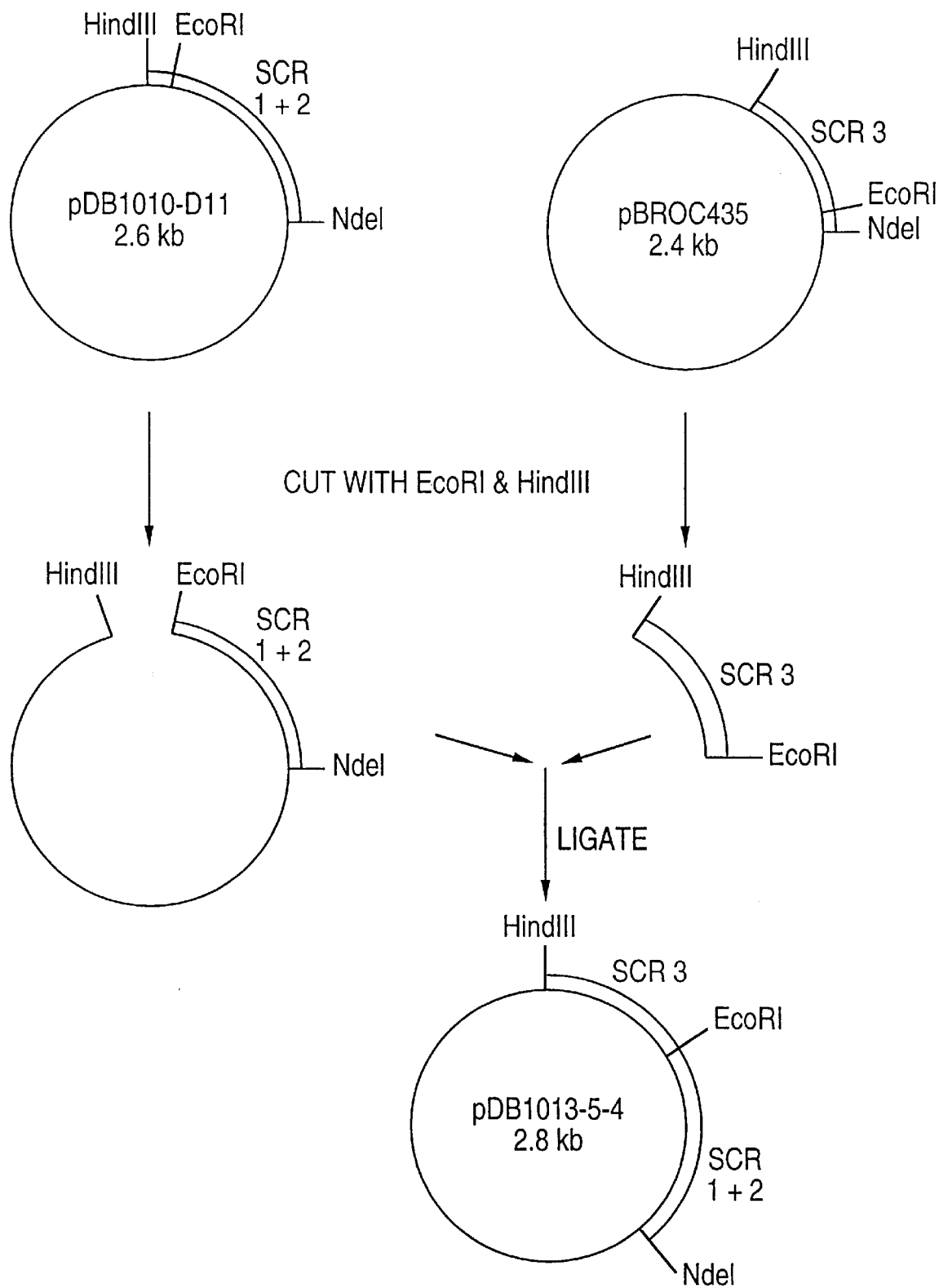
FIG. 2 illustrates the construction from pDB1010-D11 and pBROC435 of plasmid pDB1013-5-4 coding for SCR 1+2+3. Plasmid sizes are approximate and are not drawn to scale.
Figure 3:
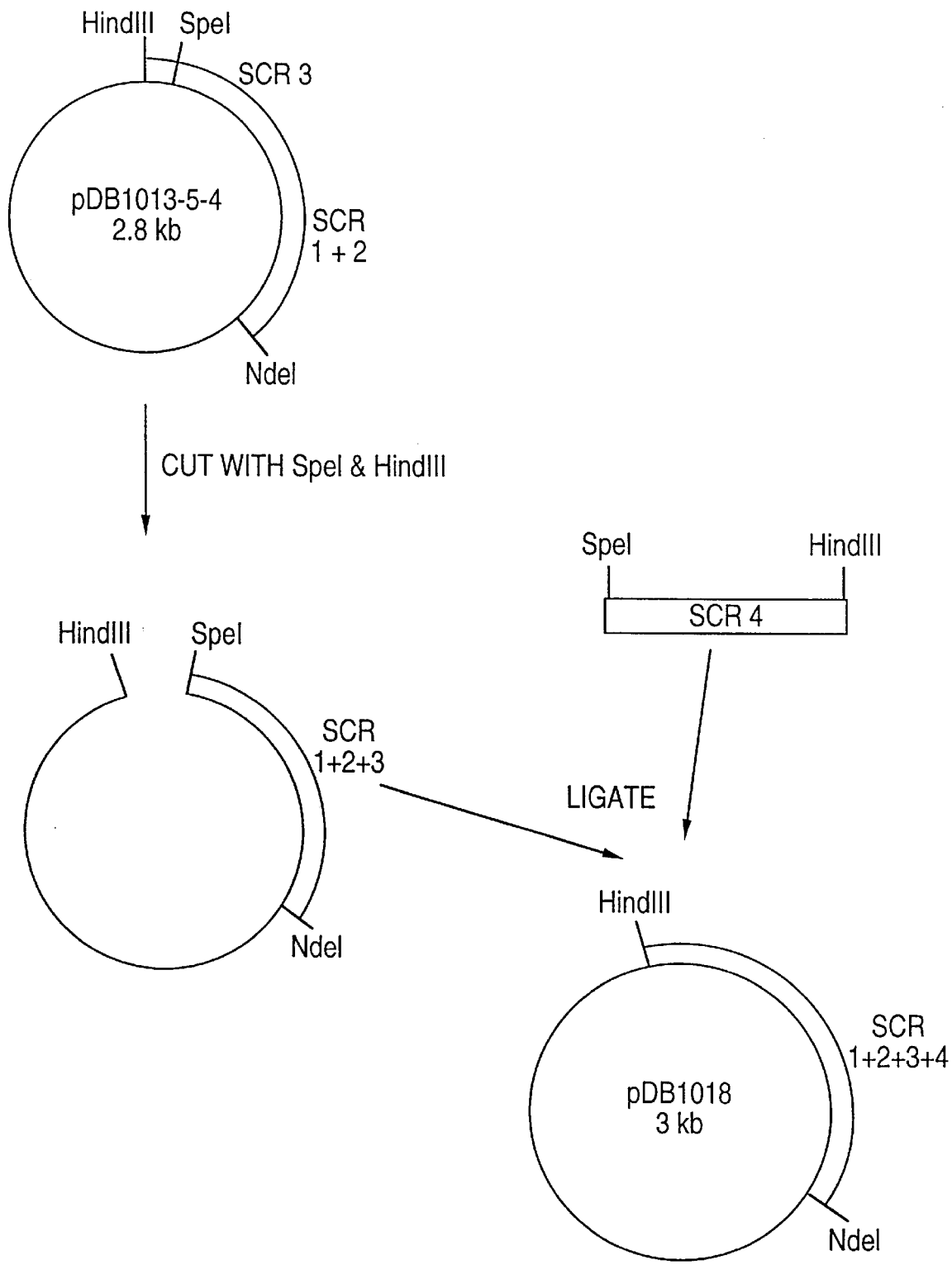
FIG. 3 illustrates the construction from pDB1013-5-4 of pDB1018 coding for SCR 1+2+3+4. Plasmid sizes are approximate and are not drawn to scale.

1. Chen G.-F. and Inouye M. (1990). Suppression of the negative effect of minor arginine codons on gene expression; preferential usage of minor codons within the first 25 codons of the E.coli genes. Nuc.Acids.Res. 18 (6): 1465–1473.

2. Dacie, J. V. & Lewis S. M., (1975) *Practical haematology* Fifth Edition, Ed. Churchill Livingstone, Edinburgh & New York pp 3–4

3. Devereux, Haeberli and Smithies (1984). A comprehensive set of sequence analysis programmes for the vax. Nuc.Acids.Res. 12(1): 387–395

4. Hourcade D., Miesner D. R., Atkinson J. P. & Holers V. M. (1988). Identification of an alternative polyadenylation site in the human C3b/C4b receptor (complement receptor type 1) transcriptional unit and prediction of a secreted form of complement receptor type 1. *J. Exp. Med.* 168 1255–1270

5. Low B. (1968). Proc.Natl.Acad.Sci.USA 60:160

6. Sambrook J., Fritsch E. F. and Maniatis J. (1989). Molecular Cloning: A Laboratory Manual 2nd Edition. Cold Spring Harbour Laboratory Press 7. Studier F. W. and Moffat B. A. (1986). J.Mol.Biol. 189: 113

8. Tabor S. (1990). Expression using the T RNA polymerase/promoter system. In Current Protocols in Molecular Biology (F. A. Ausubel, R. Brent, R. E. Kingston, .D. D. Moore, J. G. Seidman, J. A. Smith and K. Struhl, eds) pp. 16.2.1–16.2.11 Greene Publishing and Wiley-lnterscience, New York

TABLE 1

| |
|---|
| OLIGO 1 = SEQ ID NO: 1 |
| OLIGO 2 = SEQ ID NO: 2 |
| OLIGO 3 = SEQ ID NO: 3 |
| OLIGO 4 = SEQ ID NO: 4 |
| OLIGO 5 = SEQ ID NO: 5 |
| OLIGO 6 = SEQ ID NO: 6 |
| OLIGO 7 = SEQ ID NO: 7 |
| OLIGO 8 = SEQ ID NO: 8 |
| OLIGO 9 = SEQ ID NO: 9 |
| OLIGO 10 = SEQ ID NO: 10 |
| OLIGO 11 = SEQ ID NO: 11 |
| OLIGO 12 = SEQ ID NO: 12 |
| OLIGO 13 = SEQ ID NO: 13 |
| OLIGO 14 = SEQ ID NO: 14 |
| OLIGO 15 = SEQ ID NO: 15 |
| OLIGO 16 = SEQ ID NO: 16 |
| OLIGO 17 = SEQ ID NO: 17 |
| OLIGO 18 = SEQ ID NO: 18 |
| OLIGO 19 = SEQ ID NO: 19 |
| OLIGO 20 = SEQ ID NO: 20 |
| OLIGO 21 = SEQ ID NO: 21 |
| OLIGO 22 = SEQ ID NO: 22 |
| OLIGO 23 = SEQ ID NO: 23 |
| OLIGO 24 = SEQ ID NO: 24 |
| OLIGO 25 = SEQ ID NO: 25 |
| OLIGO 26 = SEQ ID NO: 26 |

TABLE 2

Amino acid sequences of proteins, deduced from the cDNA constructs.

The full deduced sequence of the proteins of the Examples are given as follows:
MQ1—>K196 of CR-1 is given in SEQ ID NO: 27
MR122—>K196 of CR-1 is given in SEQ ID NO: 28
MQ1-S253 of CR-1 is given in SEQ ID NO: 29
The R235H mutant of MQ1-S253 of CR-1 is given in SEQ ID NO: 30
MR122-S253 of CR-1 is given in SEQ ID NO: 31.

---

We claim:

1. A soluble polypeptide comprising no more than three short consensus repeats (SCR) of long homologous repeat A of Complement Receptor 1, wherein the polypeptide comprises SCR3 and at least one repeat selected from the group consisting of SCR1, SCR2, and SCR4.

2. A soluble polypeptide comprising no more than one short consensus repeat (SCR) of long homologous repeat A of Complement Receptor 1, wherein the polypeptide comprises SCR3.

3. A soluble polypeptide that can inhibit complement activation and that comprises no more than three short consensus repeats (SCR) of long homologous repeat A of Complement Receptor 1, wherein the soluble peptide is obtainable by expressing in a host cell a DNA molecule encoding the soluble polypeptide to produce the soluble polypeptide, wherein the DNA molecule encodes SCR3 and at least one repeat selected from the group consisting of SCR1, SCR2, and SCR4; and harvesting the soluble polypeptide.

4. A soluble polypeptide that can inhibit complement activation and that comprises no more than one short consensus repeat (SCR) of long homologous repeat A of Complement Receptor 1, wherein the soluble peptide is obtainable by expressing in a host cell a DNA molecule encoding SCR3 to produce the soluble polypeptide; and harvesting the soluble polypeptide.

5. A soluble polypeptide according to claim 3, wherein the host cell is a bacterium.

6. A soluble polypeptide according to claim 4, wherein the host cell is a bacterium.

7. A soluble polypeptide according to claim 1, wherein the polypeptide comprises three SCRs.

8. A soluble polypeptide according to claim 3, wherein the polypeptide comprises three SCRs.

9. A pharmaceutical composition for inhibiting complement activation, comprising a soluble polypeptide comprising no more than three short consensus repeats (SCR) of long homologous repeat A of Complement Receptor 1, wherein the polypeptide comprises SCR3 and at least one repeat selected from the group consisting of SCR1, SCR2, and SCR4.

10. A pharmaceutical composition for inhibiting complement activation, comprising a soluble polypeptide comprising no more than one short consensus repeat (SCR) of long homologous repeat A of Complement Receptor 1, wherein the polypeptide comprises SCR3.

11. A pharmaceutical composition for inhibiting complement activation, comprising a soluble polypeptide comprising no more than three short consensus repeats (SCR) of long homologous repeat A of Complement Receptor 1, wherein the soluble polypeptide is obtainable by expressing in a host cell a DNA molecule encoding SCR3 and at least one repeat selected from the group consisting of SCR1, SCR2, and SCR4 in order to produce the soluble protein; and harvesting the soluble polypeptide.

12. A pharmaceutical composition for inhibiting complement activation comprising a soluble polypeptide comprising no more than one short consensus repeat (SCR) of long homologous repeat A of Complement Receptor 1, wherein the soluble polypeptide is obtainable by expressing in a host cell a DNA molecule encoding SCR3 in order to produce the soluble polypeptide; and harvesting the soluble polypeptide.

13. A pharmaceutical composition according to claim 11, wherein the host cell is a bacterium.

14. A pharmaceutical composition according to claim 12, wherein the host cell is a bacterium.

15. A method of treating a patient in need of inhibition of complement activation, comprising administering to the patient a soluble polypeptide comprising no more than three short consensus repeats (SCR) of long homologous repeat A of Complement Receptor 1, wherein the polypeptide comprises SCR3 and at least one repeat selected from the group consisting of SCR1, SCR2, and SCR4.

16. A method of treating a patient in need of inhibition of complement activation, comprising administering to the patient a soluble polypeptide comprising no more than one short consensus repeat (SCR) of long homologous repeat A of Complement Receptor 1, wherein the polypeptide comprises SCR3.

* * * * *